(12) United States Patent
Semizarov et al.

(10) Patent No.: US 8,742,083 B1
(45) Date of Patent: Jun. 3, 2014

(54) PANEL OF MICRORNAS THAT SILENCE THE MCL-1 GENE AND SENSITIZE CANCER CELLS TO ABT-263

(75) Inventors: Dimitri Semizarov, Chicago, IL (US); Xin Lu, Libertyville, IL (US); Lloyd T. Lam, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 451 days.

(21) Appl. No.: 12/978,086

(22) Filed: Dec. 23, 2010

Related U.S. Application Data

(60) Provisional application No. 61/291,208, filed on Dec. 30, 2009.

(51) Int. Cl.
*C12Q 1/68* (2006.01)
*C07H 21/02* (2006.01)
*C07H 21/04* (2006.01)

(52) U.S. Cl.
USPC ........ 536/23.1; 536/24.3; 536/24.33; 435/6.1

(58) Field of Classification Search
USPC ............................ 536/23.1, 24.3, 24.33, 24.5
See application file for complete search history.

(56) References Cited

PUBLICATIONS

Lam et al. (Molecular Cancer Therapeutics, 2010 vol. 9(11):2943-2950).*
Ausubel F.M., et al., "Preparation and Analysis of DNA," in: Current Protocols in Molecular Biology, John Wiley & Sons, Inc., 1998, Table of Contents.
Baek D., et al., "The Impact of MicroRNAs on Protein Output," Nature, 2008, vol. 455, pp. 64-71.
Bartel D.P., "MicroRNAs: Target Recognition and Regulatory Functions," Cell, 2009, vol. 136, pp. 215-233.
Betel D., et al., "The MicroRNA.org: Resource: Targets and Expression," Nucleic Acids Research, 2008, vol. 36, pp. D149-D153.
Cheng C., et al., "Inferring MicroRNA Activities by Combining Gene Expression with MicroRNA Target Prediction," PLoS One, 2008, vol. 3 (4), pp. e1989.
Craig R.W., "MCL1 Provides a Window on the Role of the BCL2 Family in Cell Proliferation, Differentiation and Tumorigenesis," Leukemia, 2002, vol. 16 (4), pp. 444-454.
Crawford M., et al., "MicroRNA 133B Targets Pro-survival Molecules MCL-1 and BCL2L2 in Lung Cancer," Biochemical and Biophysical Research Communications, 2009, vol. 388, pp. 483-489.
Esquela-Kerscher A., et al., "The Let-7 MicroRNA Reduces Tumor Growth in Mouse Models of Lung Cancer," Cell Cycle, 2008, vol. 7 (6), pp. 759-764.
Farh K.K., et al., "The Widespread Impact of Mammalian MicroRNAs on mRNA Repression and Evolution," Science, 2005, vol. 310, pp. 1817-1821.
Grimson A., et al., "MicroRNA Targeting Specificity in Mammals: Determinants Beyond Seed Pairing," Molecular Cell, 2007, vol. 27, pp. 91-105.
John B., et al., "Human MicroRNA Targets," PLoS Biology, 2004, vol. 2 (11), pp. e363.
Kertesz M., et al., "The Role of Site Accessibility in MicroRNA Target Recognition," Nature Genetics, 2007, vol. 39 (10), pp. 1278-1284.

(Continued)

*Primary Examiner* — Terra Cotta Gibbs
(74) *Attorney, Agent, or Firm* — Lisa V. Mueller; Michael Best & Friedrich LLP

(57) ABSTRACT

MicroRNAs (miRNAs) that sensitize cancer cells to Bcl-2 family protein inhibitors are identified and described. Oligonucleotide panels, arrays and methods using the sensitizing miRNAs are also disclosed.

9 Claims, 14 Drawing Sheets

(56) References Cited

PUBLICATIONS

Kota J., et al., "Therapeutic MicroRNA Delivery Suppresses Tumorigenesis in a Murine Liver Cancer Model," Cell, 2009, vol. 137, pp. 1005-1017.

Kumar M.S., et al., "Impaired MicroRNA Processing Enhances Cellular Transformation and Tumorigenesis," Nature Genetics, 2007, vol. 39 (5), pp. 673-677.

Lewis B.P., et al., "Conserved Seed Pairing, Often Flanked by Adenosines, Indicates that Thousands of Human Genes are MicroRNA Targets," Cell, 2005, vol. 120, pp. 15-20.

Lewis B.P., et al., "Prediction of Mammalian MicroRNA Targets," Cell, 2003, vol. 115, pp. 787-798.

Lim L.P., et al., "Microarray Analysis Shows that Some MicroRNAs Downregulate Large Numbers of Target mRNAs," Nature, 2005, vol. 433, pp. 769-773.

Lin X., et al., "'Seed' Analysis of Off-Target siRNAs Reveals an Essential Role of Mcl-1 in Resistance to the Small-molecule Bcl-2/Bcl-XL Inhibitor ABT-737," Oncogene, 2007, vol. 26, pp. 3972-3979.

Lu J., et al., "MicroRNA Expression Profiles Classify Human Cancers," Nature, 2005, vol. 435, pp. 834-838.

Mendes N.D., et al., "Current Tools for the Identification of miRNA Genes and their Targets," Nucleic Acids Research, 2009, vol. 37 (8), pp. 2419-2433.

Mott J.L., et al., "Mir-29 Regulates Mcl-1 Protein Expression and Apoptosis," Oncogene, 2007, vol. 26, pp. 6133-6140.

Oltersdorf T., et al., "An Inhibitor of Bcl-2 Family Proteins Induces Regression of Solid Tumours," Nature, 2005, vol. 435, pp. 677-681.

Rehmsmeier M., et al., "Fast and Effective Predition of MicroRNA/target Duplexes," Bioinformatics, 2004, vol. 10, pp. 1507-1517.

Robins H., et al., "Incorporating Structure to Predict MicroRNA Targets," Proceedings of the National Academy of Sciences, 2005, vol. 102 (11), pp. 4006-4009.

Sambrook J., et al., "Molecular Cloning-A Laboratory Manual," 1989, 2nd Ed., Cold Spring Harbor Laboratory Press, Table of Contents.

Selbach M., et al., "Widespread Changes in Protein Synthesis Induced by MicroRNAs," Nature, 2008, vol. 455, pp. 58-63.

Sethupathy P., et al., "A Guide Through Present Computational Approaches for the Identification of Mammalian MicroRNA Targets," Nature Methods, 2006, vol. 3 (11), pp. 881-886.

Su H., et al., "MicroRNA-101, Down-regulated in Hepatocellular Carcinoma, Promotes Apoptosis and Suppresses Tumorigenicity," Cancer Research, 2009, vol. 69 (3), pp. 1135-1142.

Tahir S.K., et al., "Influence of Bcl-2 Family Members on the Cellular Response of Small-Cell Lung Cancer Cell Lines to ABT-737," Cancer Research, 2007, vol. 67 (3), pp. 1176-1183.

Tse, C. et al., "ABT-263: A Potent and Orally Bioavailable Bcl-2 Family Inhibitor," Cancer Research, 2008, vol. 68 (9), pp. 3421-3428—Including Supplementary Data.

Xu J., et al., "Down-regulations of B-cell Lymphoma 2 and Myeloid Cell Leukemia Sequence 1 by MicroRNA 153 Induce Apoptosis in a Glioblastoma Cell Line DBTRG-05MG," International Journal of Cancer, 2009, vol. 126, pp. 1029-1035.

\* cited by examiner

A
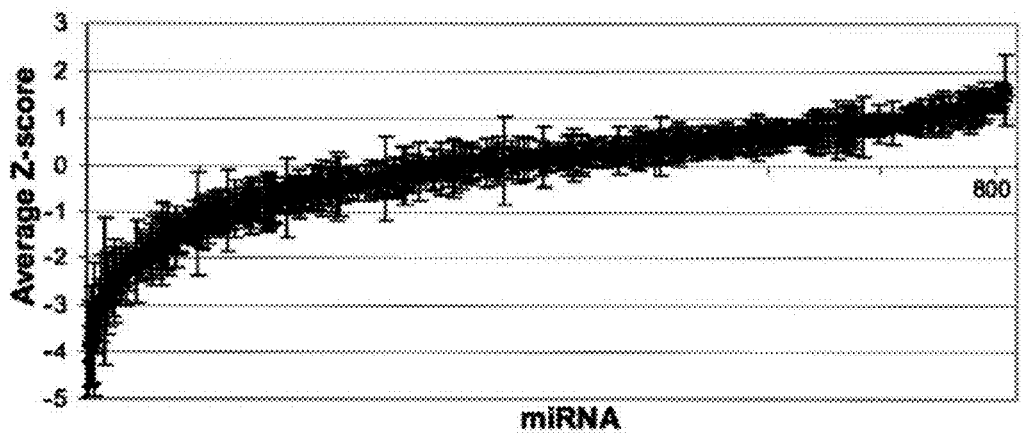
B
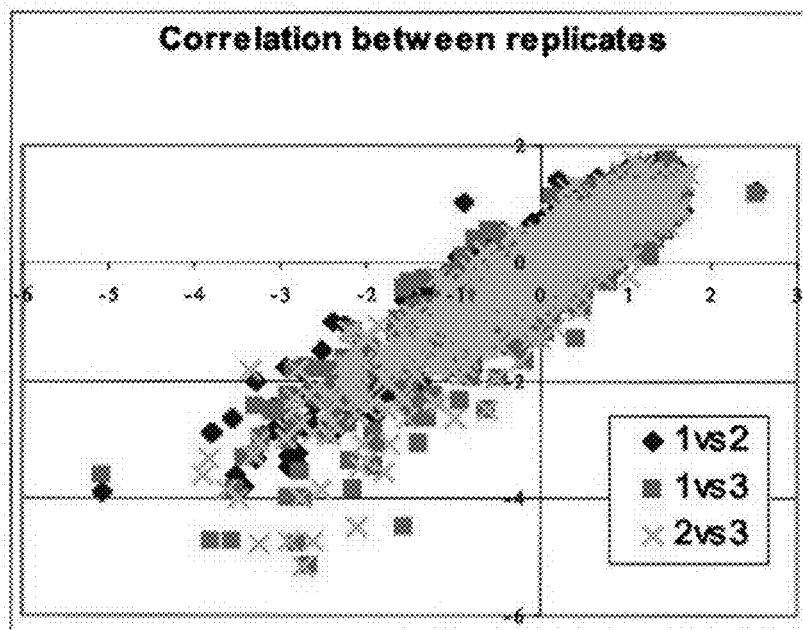
FIG. 5A-B

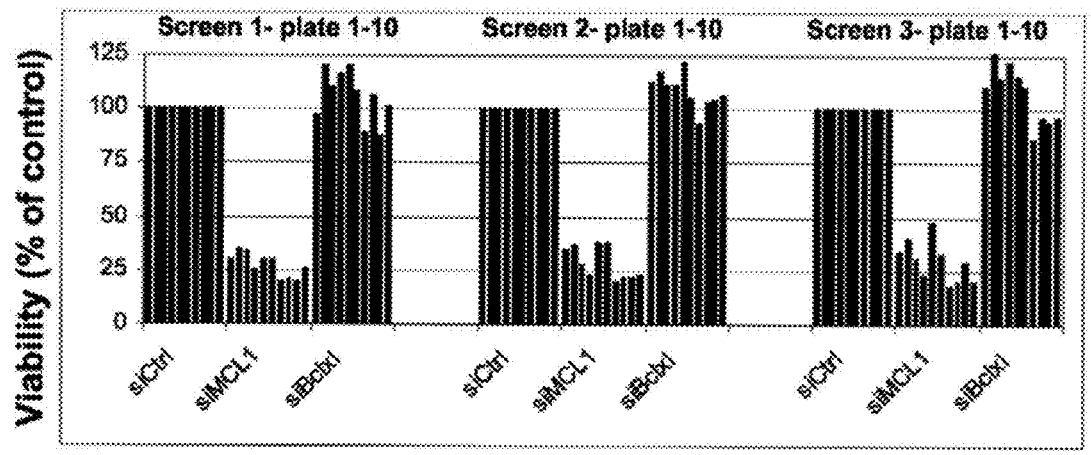
C
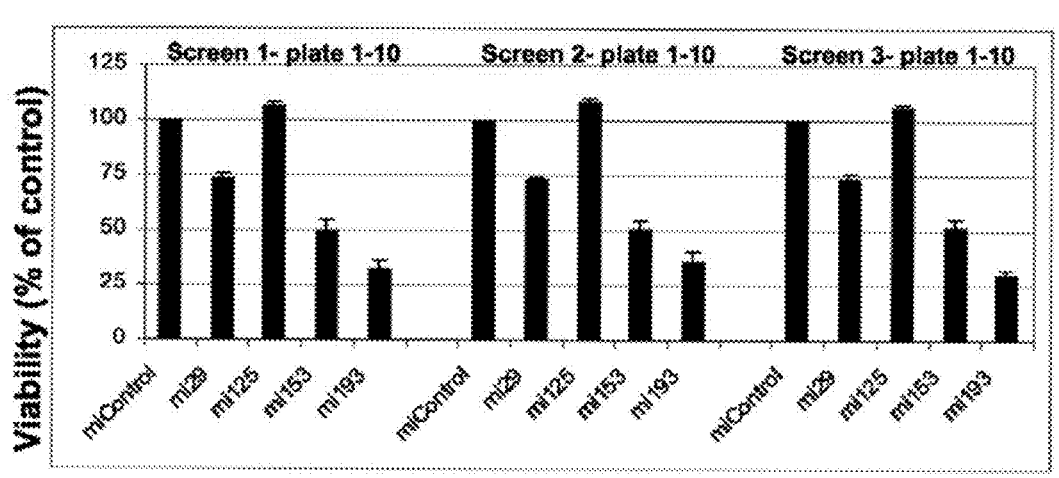
D
FIG. 5C-D

PANEL OF MICRORNAS THAT SILENCE THE MCL-1 GENE AND SENSITIZE CANCER CELLS TO ABT-263

RELATED APPLICATION INFORMATION

This application is a non-provisional of U.S. Patent Application No. 61/291,208, entitled Micrornas That Sensitize Cells to BCL-2. Family Protein Inhibitors, filed on Dec. 30, 2009, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 28, 2011, is named 10302USO.txt and is 10,778 bytes in size.

TECHNICAL FIELD

The present disclosure relates generally to the treatment of cancer and in particular to compositions and methods useful in evaluating the effectiveness of particular therapeutic compounds.

BACKGROUND

A hallmark of cancer cells is deregulation of the apoptotic cell death program. One mechanism to deregulate apoptosis is by overexpressing the antiapoptotic members of the Bcl-2 family of proteins, Bcl-2, Bcl-xl, Bcl-w, A1, and Mcl-1. To restore the ability of cells to undergo apoptosis, small molecules have been designed to inhibit these proteins. ABT-263 is a first-in-class Bcl-2 inhibitor with a high affinity for Bcl-2, Bcl-xl, and Bcl-w. It exhibits potent activity as a single agent against several tumor types. However, most solid tumors are resistant to ABT-263 due to high expression of Mcl-1, to which the drug has a low affinity. Mcl-1 is known to be regulated transcriptionally, translationally, and by proteosome-mediated degradation, and microRNA (miRNA) may also play a role.

MiRNAs are small non-coding RNAs that regulate global gene expression by binding to the 3' UTRs of their target genes and repressing translation. Many of these small RNAs are expressed at abnormal levels in multiple cancer types. Since miRNAs can regulate hundreds of targets, and each gene can be regulated by hundreds of miRNAs, the identification of miRNA targets has been a challenge. Multiple tools are available for identifying miRNA targets. In general, the criteria for miRNA target identification are (i) the presence of a sequence at the 5' end of miRNA complementary to the 3'UTR of the mRNA, (ii) favorable thermodynamic hybridization between miRNA and mRNA, (iii) conservation of the miRNA target sites across multiple species, (iv) site context that increases site efficacy (such as AU-rich nucleotide composition near the site, proximity to sites for co-expressed miRNAs, proximity to residues pairing to miRNA nucleotides 13-16, positioning within the 3'-UTR at least 15 nt from the stop codon, and positioning away from the center of long UTRs), (v) miRNA expression versus target gene expression data, and (vi) secondary structure of the target that is conducive to miRNA binding. Unfortunately, the current target prediction tools are unreliable, resulting in a large number of false positives and false negatives. Recently, proteomics has also been employed to facilitate the identification of miRNA targets.

SUMMARY

In one aspect, the present disclosure provides a panel of oligonucleotide primers or probes for determining an miRNA profile in a biological sample, the panel comprising at least two miRNA primers or probes, each primer or probe capable of selectively binding one of at least two human miRNA selected from SEQ ID NOS: 1-19. In an exemplary embodiment, the human miRNA may be selected from the group consisting of SEQ ID NOS: 1-12. In another exemplary embodiment, the human miRNA may be selected from the group consisting of SEQ ID NOS: 1-10. The panel of primers or probes may further be immobilized on the solid support to form an array. The solid support may comprise, for example, one or more components selected from the group consisting of: a membrane, a chip, a disk, a strip, a filter, a microsphere, a slide, a multi-well plate, a bead, or an optical fiber.

In another aspect, the present disclosure provides a method for evaluating the sensitivity of a subject to treatment with a Bcl-2 family inhibitor, the method comprising the steps of (a) in a biological sample taken from the subject, determining expression levels of at least one miRNA selected from the group consisting of SEQ ID NOS: 1-19; and (b) evaluating the sensitivity of the subject to treatment with a Bcl-2 family protein inhibitor based on the expression levels of the at least one miRNA. In an exemplary embodiment, the one or more miRNA are selected from the group consisting of SEQ ID NOS: 1-12. In another exemplary embodiment, the one or more miRNA are selected from the group consisting of SEQ ID NOS: 1-10. In an embodiment of the above method, increased expression levels of the miRNA relative to a normal control are taken as indicative of sensitivity of the subject to treatment with the Bcl-2 family inhibitor. The method may further comprise obtaining a biological sample from the subject. In the method, expression of the miRNA may be determined by an amplification assay or a hybridization assay. The method may comprise using one or more oligonucleotide primers or probes that selectively bind to the miRNA to detect the miRNA. When such oligonucleotide primers or probes are used, the method may further comprise labeling miRNA from the sample, and may still further comprise hybridizing the labeled miRNA to one or more of the oligonucleotide primers or probes. The method may further comprise using real-time quantitative PCR or a branched DNA assay to determine the expression levels of the miRNA. In the above method, the subject may be a human subject, i.e. a patient suspected of having a cancer or at risk for a cancer recurrence. The method may further comprise comparing miRNA expression levels in the sample to miRNA expression levels in a normal reference sample. The reference sample may be a biological sample from a second human subject, or a biological sample taken from the human subject being evaluated. In the method, the biological sample may be selected from the group consisting of: a cell lysate, a cell culture, a cell line, a tissue, a biological fluid, a blood sample, a serum sample, a plasma sample, a urine sample, and a skin sample. The biological sample may be a tissue sample. The biological sample may be fresh, frozen, fixed, or paraffin-embedded, such as for example a formalin-fixed, paraffin-embedded (FFPE) tissue. In the method, the Bcl-2 family protein inhibitor can be selected from the group consisting of ABT-737, ABT-263, ABT-199, a Bcl-2 selective inhibitor, a Bcl-XL selective inhibitor and any combination thereof. In an exemplary embodiment of the method, the Bcl-2 family protein inhibitor is ABT-263.

In another aspect, the present disclosure provides a kit useful for assaying miRNA expression levels in a biological sample of a subject, the kit comprising: a) a panel of two or more oligonucleotide primers or probes, each primer or probe capable of selectively binding a human miRNA selected from Table 1, especially an miRNA selected from SEQ ID NOS: 1-19; b) one or more reagents for amplifying the miRNA present in the biological sample using the primers or probes; and c) instructions for quantifying expression levels of the miRNA in the biological sample and evaluating the sensitivity of the subject to treatment with a Bcl-2 family protein inhibitor based on the expression levels of the miRNA. In an exemplary embodiment of the kit, the one or more miRNAs are selected from the group consisting of SEQ ID NOS: 1-12. In another exemplary embodiment of the kit, the one or more miRNAs are selected from the group consisting of SEQ ID NOS: 1-10. The kit may further comprise a solid support, wherein the probes or primers comprise probes immobilized on the solid support. The solid support may comprise one or more components selected from the group consisting of: a membrane, a chip, a disk, a strip, a filter, a microsphere, a slide, a multiwell plate, a bead, or an optical fiber. In the kit, the biological sample may be selected from the group consisting of: a cell lysate, a cell culture, a cell line, a tissue, a biological fluid, a blood sample, a serum sample, a plasma sample, a urine sample, and a skin sample. The one or more reagents may comprise one or more miRNA hybridization or amplification reagents for any two or more of the miRNAs.

In another aspect, the present disclosure provides a method for determining whether an miRNA increases sensitivity of a subject to treatment with a Bcl-2 family inhibitor, the method comprising: a) reverse transfecting a population of cancer cells with the candidate miRNA; b) contacting the cells with an effective amount of the Bcl-2 family inhibitor, and c) determining the survival rate of the cells, wherein a decrease in cell survival rate is indicative that the miRNA increases sensitivity of the subject to treatment with the Bcl-2 family inhibitor.

In another aspect, the present disclosure provides a method for determining whether an miRNA increases sensitivity of a subject to treatment with a Bcl-2 family inhibitor, the method comprising: a) reverse transfecting a population of cancer cells with the candidate miRNA; b) contacting the cells with an effective amount of the Bcl-2 family inhibitor, and c) determining Mcl-1 expression level in the cells, wherein a decrease in Mcl-1 expression is indicative that the miRNA increases sensitivity of the subject to treatment with the Bcl-2 family inhibitor. In either of the methods for determining whether an miRNA increases sensitivity of a subject to treatment with a Bcl-2 family inhibitor, the population of cancer cells may comprise HCT-116 cells or CHL1 cells.

In another aspect, the present disclosure provides a method for treating a human subject having or suspected of having a cancer, the method comprising administering to the subject a therapeutic amount of a Bcl-2 family protein inhibitor and an amount of at least one sensitizing miRNA, especially at least one miRNA selected from the group of SEQ ID NOS: 1-19, or of at least one siRNA of 19-24 bp having a sequence identical to any 19-24 contiguous by of the miRNA, wherein the amount of the at least one miRNA or siRNA is sufficient to sensitize the subject to treatment with the Bcl-2 family protein inhibitor. In an exemplary embodiment of the method, the one or more miRNAs are selected from the group consisting of SEQ ID NOS: 1-12. In another exemplary embodiment of the method, the one or more miRNAs are selected from the group consisting of SEQ ID NOS: 1-10.

In another aspect, the present disclosure provides a method for re-sensitizing a human subject having or suspected of having acquired resistance to treatment of a cancer with a Bcl-2 family protein inhibitor, the method comprising administering to the subject an amount of at least one sensitizing miRNA, especially at least one miRNA selected from the group consisting of SEQ ID NOS: 1-19, or of at least one siRNA of 19-24 bp having a sequence identical to any 19-24 contiguous base pairs of the miRNA, wherein the amount of the at least one miRNA or siRNA is sufficient to re-sensitize the subject to treatment with the Bcl-2 family protein inhibitor. In an exemplary embodiment of the method, the one or more miRNAs may be selected from the group consisting of SEQ ID NOS: 1-12. In another exemplary embodiment of the method, the one or more miRNAs are selected from the group consisting of SEQ ID NOS: 1-10.

In any of the above methods, the Bcl-2 family protein inhibitor may be selected from the group consisting of ABT-737, ABT-263, ABT-199, a Bcl-2 selective inhibitor, a Bcl-XL selective inhibitor and any combination thereof, and in exemplary embodiments of each method the Bcl-2 family protein inhibitor is ABT-263.

In another aspect, the present disclosure provides a method of promoting apoptosis in a cell comprising decreasing the amount of the Mcl-1 protein in the cell by contacting the cell with an amount of at least one miRNA selected from the group consisting of SEQ ID NOS: 1-12, or of at least one siRNA of 19-24 bp having a sequence identical to any 19-24 contiguous by of the miRNA, or a combination thereof, wherein the amount of the at least one miRNA or siRNA is sufficient to decrease the amount of the Mcl-1 protein in the subject. In an exemplary embodiment of the method, the one or more miRNAs are selected from the group consisting of SEQ ID NOS: 1-10.

BRIEF DESCRIPTION OF THE DRAWINGS

FIG. 5A is a scatter plot of averaged Z-scores from the ABT-263 sensitization screen carried out in triplicate with ABT-263.

FIG. 5B is a plot of the correlation of ABT-263 sensitivity Z-scores of the three replicates of the screen, showing reproducibility of the screen.

FIG. 5C is a bar graph of percentage of surviving HCT-116 cells for control, Mcl-1, and Bcl-xl siRNA transfections used as controls in the screens.

FIG. 5D is a bar graph of percentage of surviving HCT-116 cells after transfection with miControl, miR-29, miR-125, miR-153, and miR-193 transfections used as controls in the screens.

FIG. 8 shows results of in silico prediction of binding of the top miRNA hits to Mcl-1 3'UTR by TargetScan, miRANDA, or seed sequence analysis. FIG. 8 discloses the 3' to 5' sequences as SEQ ID NOS 2, 6, 9, 1, 3, 10, 8, 4, 4, 4, 7, 5, 12 and 11 and the 5' to 3' sequences as SEQ ID NOS 31-44, respectively, in order of appearance.

DETAILED DESCRIPTION

Figure 1A:
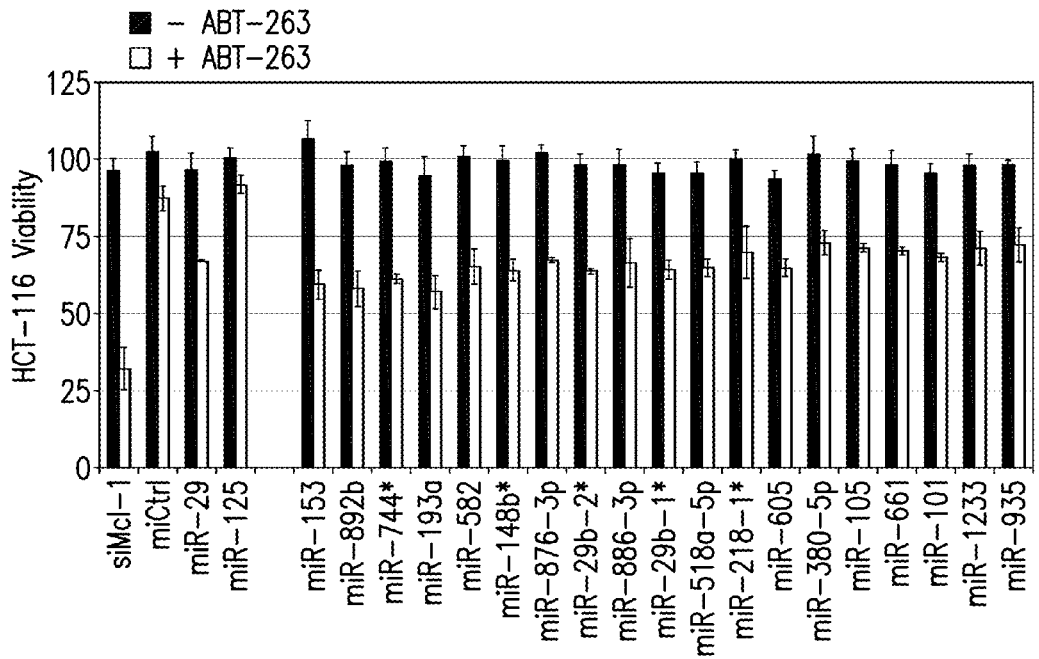
FIG. 1A is a bar graph showing results of a Bcl-2 inhibitor sensitization screen of an miRNA library, showing modulation of HCT-116 cell sensitivity to ABT-263 in cells transfected with sensitizing miRNA.

The present disclosure is based on the surprising finding that miRNAs can sensitize cancer cells to a Bcl-2 family protein inhibitor, such that cells previously resistant to the Bcl-2 family protein inhibitor become sensitized and undergo apoptosis. The results further indicate that most of the miRNAs shown to have such an effect do so at least in part by down-regulating Mcl-1 expression, and thus indirectly Mcl-1 activity. Among other aspects, these findings can be used as a basis for assays of sensitivity to Bcl-2 family protein inhibitors and for therapies to increase sensitivity of tumors to Bcl-2 family inhibitors.

A. Definitions

Section headings as used in this section and the entire disclosure herein are not intended to be limiting.

a) As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

b) Bcl-2

As used herein, "Bcl-2" (official symbol BCL2) means the human B-cell CLL/lymphoma 2 gene; "Bcl-xl" (official symbol BCL2L1) means the human BCL2-like 1 gene; and the proteins encoded thereby. As used herein, the term "official symbol" refers to that used in the EntrezGene database maintained by the United States National Center for Biotechnology Information.

c) Bcl-2 Family Protein Inhibitor

As used herein, a "Bcl-2 family protein inhibitor" refers to a therapeutic compound of any type, including small molecule-, antibody-, antisense-, small interfering RNA-, or microRNA-based compounds, that binds to a Bcl-2 family nucleic acid or protein, and antagonizes the activity of the nucleic acid or protein.

d) Mcl-1

As used herein, the term "Mcl-1" (official symbol Mcl-1) means the myeloid cell leukemia sequence 1 gene, and the protein encoded thereby, wherein the term "official symbol" again refers to that used in the EntrezGene database maintained by the United States National Center for Biotechnology Information.

e) miRNA

As used interchangeably herein, the terms "microRNA" and "miRNA" refer to non-coding single-stranded RNA molecules of 21-24 nucleotides in length and having a nucleotide sequence that is complementary in whole or in part to one or more messenger RNA (mRNA) molecules.

f) Sample

As used herein, the term "sample" generally refers to a biological material being tested for and/or suspected of containing cancer cells. The biological material may be derived from any biological source. Examples of biological materials include, but are not limited to, a cell lysate, a cell culture, a cell line, a tissue, a biological fluid, a blood sample, a serum sample, a plasma sample, a urine sample, and a skin sample, fresh frozen tissue sample, a paraffin embedded tissue sample or an extract or processed sample produced from any of a peripheral blood sample, a serum or a plasma fraction of a blood sample. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the sample, such pretreatment methods are such that cancer cells remain in the sample.

g) siRNA

As used herein, the term "siRNA" refers to short (19-24 bp, usually 21-22 bp in length) double-stranded RNA molecules that can be used to down-regulate expression of a specific gene, a portion of which is complementary to the sequence of the siRNA.

B. MicroRNAs (MiRNAs), Uses Thereof and Kits

Sensitizing miRNA Panels

Table 1 lists sensitizing all miRNAs that were validated as sensitizers to Bcl-2 family protein inhibitors in HCT116 and/or CHL1 cells according to the present disclosure, and their sequences. The stem-loop structure of each of these can be found by accessing the miRBase Sequence database and Registry at http://www.mirbase.org/. SEQ ID NOS: 1-19 were validated as strong sensitizers in HCT116 and/or CHL1 cells. SEQ ID NOS: 1-12 were shown to decrease Mcl-1 protein expression in HCT116 and CHL1 cells, and SEQ ID NOS: 1-10 were shown to bind directly to Mcl-1 3'UTR. Table 2 lists control miRNAs, an Mcl-1 targeting siRNA, and their nucleotide sequences according to the present disclosure.

TABLE 1

| SEQ ID NO: | miRNA | Sequence |
| --- | --- | --- |
| 1 | miR-153 | UUGCAUAGUCACAAAAGUGAUC |
| 2 | miR-892b | CACUGGCUCCUUUCUGGGUAGA |
| 3 | miR-193a | AACUGGCCUACAAAGUCCCAGU |
| 4 | miR-582 | UUACAGUUGUUCAACCAGUUACU |
| 5 | miR-148b* | AAGUUCUGUUAUACACUCAGGC |
| 6 | miR-876-3p | UGGUGGUUUACAAAGUAAUUCA |
| 7 | miR-886-3p | CGCGGGUGCUUACUGACCCUU |
| 8 | miR-518a-5p | CUGCAAAGGGAAGCCCUUUC |
| 9 | miR-101 | UACAGUACUGUGAUAACUGAA |
| 10 | miR-661 | UGCCUGGGUCUCUGGCCUGCGCGU |
| 11 | miR-605 | UAAAUCCCAUGGUGCCUUCUCCU |
| 12 | miR-744* | CUGUUGCCACUAACCUCAACCU |
| 13 | miR-218-1* | AUGGUUCCGUCAAGCACCAUGG |
| 14 | miR-380-5p | UGGUUGACCAUAGAACAUGCGC |
| 15 | miR-105 | UCAAAUGCUCAGACUCCUGUGGU |
| 16 | miR-29b-1* | GCUGGUUUCAUAUGGUGGUUUAGA |
| 17 | miR-29b-2* | CUGGUUUCACAUGGUGGCUUAG |
| 18 | miR-1233 | UGAGCCCUGUCCUCCCGCAG |
| 19 | miR-935 | CCAGUUACCGCUUCCGCUACCGC |
| 20 | miR-let7g* | CUGUACAGGCCACUGCCUUGC |
| 21 | miR-510 | UACUCAGGAGAGUGGCAAUCAC |
| 22 | miR-654-3p | UAUGUCUGCUGACCAUCACCUU |
| 23 | miR-28 | AAGGAGCUCACAGUCUAUUGAG |
| 24 | miR-542-3p | UGUGACAGAUUGAUAACUGAAA |
| 25 | miR-493 | UUGUACAUGGUAGGCUUUCAUU |
| 26 | miR-657 | GGCAGGUUCUCACCCUCUCUAGG |
| 27 | miR-133b | UUUGGUCCCCUUCAACCAGCUA |

TABLE 2

| SEQ ID NO: | miRNA (or siRNA) | Sequence |
| --- | --- | --- |
| 28 | siMcl-1 | GCATCGAACCATTAGCAGATT |
| 29 | miR-29b | UAGCACCAUUUGAAAUCAGUGUU |
| 30 | miR-125a | UCCCUGAGACCCUUUAACCUGUGA |

*miCtrl is a Dharmacon proprietary molecule for which sequence information is unavailable.

The human miRNAs listed in Table 1 are all sensitizing miRNAs in that each miRNA listed increases cancer cell sensitivity to treatment with a Bcl-2 family protein inhibitor, such as ABT-263. By "sensitivity" is meant an apoptotic response to exposure to a Bcl-2 family protein inhibitor or a combination of two or more such inhibitors. Cell sensitivity can be determined for example by any of a number of assays as described in detail herein, including for example determining cell survival rate following reverse transfection of cancer cells, such as HCT-116 cells or CHL1 cells, with the miRNA in the presence of and in the absence of the Bcl-2 family protein inhibitor. Sensitization by the miRNA can also be detected by determining whether cell survival rate following exposure of a cell population to a Bcl-2 family protein inhibitor decreases by a predetermined amount when the cells are transfected with the miRNA, e.g. a minimal percentage decrease in number of cells surviving. According to the present disclosure, all sensitizing miRNAs having a sequence selected from SEQ ID NOS: 1-27 were determined to sensitize cancer cells by decreasing cell viability by at least 20%, following exposure to ABT-263. All sensitizing miRNAs having a sequence selected from SEQ ID NOS: 1-19 were determined to sensitize cancer cells by decreasing cell viability by at least 25%, following exposure to ABT-263.

The sensitizing miRNAs thus can be advantageously used in articles of manufacture useful for assays of sensitivity to Bcl-2 family protein inhibitors. The sequences of the miRNAs can be used for example to generate a panel of oligonucleotides that can be used as primers or probes for determining an miRNA profile in a biological sample, wherein each primer or probe has a sequence complementary, by which is meant sufficiently complementary to the selected human miRNA to be capable of selectively binding the human miRNA, thus to determine the amount of the miRNA present in a biological sample. "Sufficiently complementary" encompasses a sequence that is fully complementary or includes one, two, three or four base mismatches relative to the miRNA.

A panel includes at least two oligonucleotide primers or probes each having a sequence complementary to a different sensitizing miRNA selected from those listed in Table 1 (SEQ ID NOS: 1-27). An exemplary panel includes at least two oligonucleotide primers or probes each having a sequence complementary to a different sensitizing miRNA selected from SEQ ID NOS: 1-19. An exemplary panel may thus include 2, 3, 4, 5, 6, 7, 8, 9, 10, 11, 12, 13, 14, 15, 16, 17, 18 or 19 different primer or probe sequences. Those miRNAs specified by SEQ ID NOS: 1-12 were also shown to decrease Mcl-1 protein expression. Those miRNAs specified by SEQ ID NOS: 1-10 were also shown to bind directly to Mcl-1. An exemplary embodiment of an oligonucleotide panel according to the present disclosure includes two or more oligonucleotide primers or probes each having a sequence complementary to any two human miRNAs selected from the group consisting of SEQ ID NO: 1-12. Another exemplary embodiment of an oligonucleotide panel according to the present disclosure includes two or more primers or probes each having a sequence complementary to any two human miRNAs selected from the group consisting of SEQ ID NO: 1-10.

Methods of synthesizing oligo- and polynucleotides of a specified sequence are well known, including sequential addition (from the 5' end to the 3' end, or from the 3' end to the 5' end) of activated monomers, which form a lengthening chain that can be for example linked to a solid support. Routine synthetic methods involve stepwise addition of activated and protected monomers under a variety of conditions depending on the particular method being used, followed by removal of specific protecting groups from protected monomers to permit the synthesis of still longer chains. Once the desired chain length is achieved, all protecting groups can be removed and the oligonucleotides then removed from the solid support for further processing, which may include purification steps. Oligonucleotides primers and probes of a specified sequence including those with specific modifications such as specific labels or methylations can be obtained from any of a number of commercial vendors, such as for example Invitrogen and Applied Biosystems. Modified primers and tagged or labeled probes can be obtained and used according to any one or more of various well known assay methodologies such as in situ hybridization including FISH, and amplification techniques such as real-time q-PCR and branched DNA assays. The panel of primers or probes may, in a non-limiting example, be combined with a solid support, wherein oligonucleotide probes are immobilized on the solid support to form an array which can be used for example for in situ hybridization. The solid support may comprise, for example, one or more components selected from the group consisting of: a membrane, a chip, a disk, a strip, a filter, a microsphere, a slide, a multiwell plate, a bead, or an optical fiber.

It will be appreciated that the capability of the oligonucleotide primers or probes to hybridize to the target sequence permits detection of miRNA in a test sample. Hybridization, or specific nucleic acid hybridization, involves annealing the oligonucleotide under conditions of "high stringency" to nucleic acids in the sample. Those oligonucleotides that are successfully annealed are subsequently then detected. High stringency conditions are determined primarily according to the method used for hybridization, the oligonucleotide length, base composition and position of mismatches (if any). Hybridization techniques include for example high stringency PCR and in situ hybridization, which can be performed with relatively short probes (about 10 to about 50 nt's long). High stringency conditions in the context of these techniques are well known in the art and described for example in AUSUBEL et al., Current Protocols in Molecular Biology, John Wiley & Sons, New York, N.Y., 1998. The miRNA may be amplified prior to further analysis using amplification methods well known in the art, such as PCR methods. Oligonucleotide primers and probes according to the present disclosure include nucleic acids of variable length and of any type including DNA, RNA and also their analogs, such as those containing modified backbones, PNA (peptide nucleic acids) and LNA (locked nucleic acids), any of which can be used as probes, primers and in microarrays (arrays) that can be used for the detection and/or amplification of specific nucleic acids. The oligonucleotide primers or probes may be single or double-stranded. In an exemplary non-limiting embodiment, the oligonucleotides are at least about 9-10 nucleotides (nt) in length.

Techniques using such primers and probes, for example to detect the presence of miRNA include PCR, ligase chain reaction, nucleic acid amplification techniques and hybridization techniques, and any combination thereof. Hybridization techniques include in situ hybridization, which can be fluorescence in situ hybridization (FISH).

Methods Using Sensitizing miRNAs

Any of the methods of the present disclosure may be applied to any known or hereafter developed Bcl-2 family protein inhibitor, a Bcl-2 selective inhibitor, a Bcl-XL selective inhibitor and any combination of two or more thereof. One exemplary Bcl-2 inhibitor is ABT-737, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobe-nzenesulfonamide, which binds to each of Bcl-2, Bcl-XL, and Bcl-w.

Another exemplary Bcl-2 inhibitor is ABT-263, N-(4-(4-((2-(4-chlorophenyl)-5,5-dimethyl-1-cyclohex-1-en-1-yl)methyl)pip-erazin-1-yl)benzoyl)-4-(((1R)-3-(morpholin-4-yl)-1-((phenylsulfanyl)methyl-)propyl)amino)-3-((trifluoromethyl)sulfonyl)benzenesulfonamide. The chemical structure of ABT-263 is

ABT-263

Another exemplary Bcl-2 family protein inhibitor is ABT-199 (4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide), having the structure:

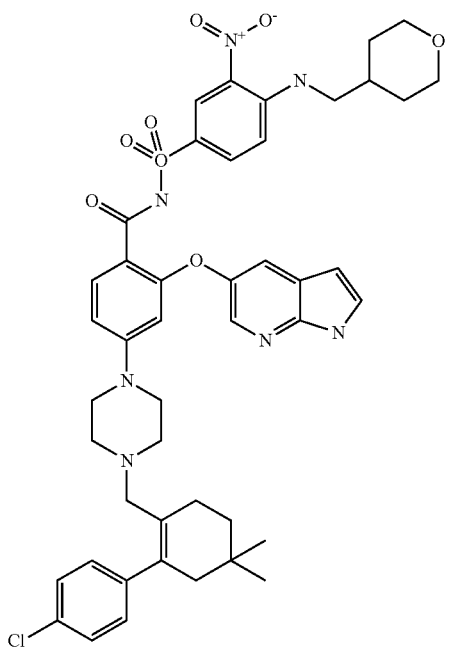

ABT-199

The methods use sensitizing miRNAs listed in Table 1, and in particular SEQ ID NOS: 1-19. Those miRNAs specified by SEQ ID NOS: 1-12 were found to decrease Mcl-1 protein expression, and those miRNAs specified by SEQ ID NOS: 1-10 were also shown to bind directly to Mcl-1. Thus, in any of the presently disclosed methods, the miRNAs may be selected more particularly from the group consisting of SEQ ID NOS: 1-19, the group consisting of SEQ ID NO: 1-12, or from the group consisting of SEQ ID NO: 1-10.

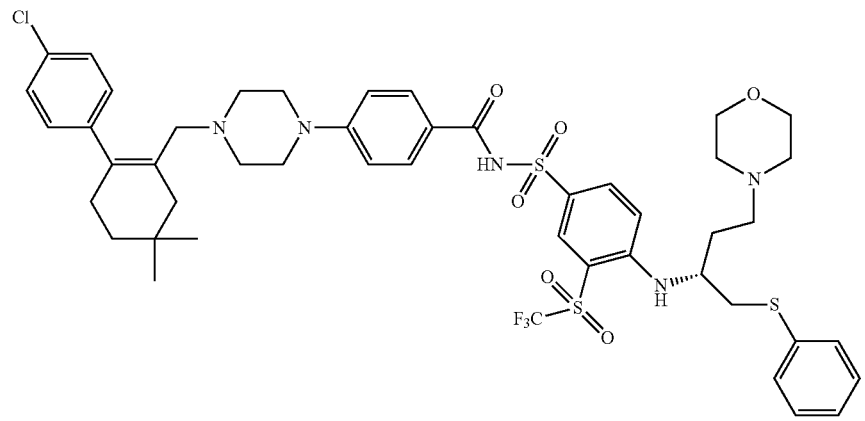 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(F)(F)F)c4)cc3)CC2)C1]

In the presently disclosed methods, the expression level of the miRNAs can be determined using any one or more assay methodologies including hybridization and amplification techniques, including but not limited to microarrays, in situ hybridization, real-time q-PCR and branched DNA assays. Oligonucleotide primers and/or probes as described above may be used in any of these methods. Expression levels of two or more sensitizing miRNAs in a biological sample provides an miRNA profile of the biological sample which can be useful, for example, in determining whether cells in the sample are sensitive to treatment with a Bcl-2 family protein inhibitor, wherein an increased level of expression of any one or more of the sensitizing miRNAs is indicative of an increased sensitivity of cells in the sample to a Bcl-2 family protein inhibitor.

The sensitizing miRNAs according to the present disclosure can also be used in a method for evaluating the sensitivity of a subject to treatment with a Bcl-2 family inhibitor. Such a method comprises, in a biological sample taken from the subject, determining expression levels of at least one sensitizing miRNA such as an miRNA selected from the group consisting of SEQ ID NOS: 1-19, and evaluating the sensitivity of the subject to treatment with a Bcl-2 family protein inhibitor based on the expression levels of the at least one miRNA. As described further in the Examples below and elsewhere herein, increased expression levels of the miRNA relative to a normal control are indicative of sensitivity of the subject to treatment with the Bcl-2 family inhibitor. The biological sample is for example a cell lysate, a cell culture, a cell line, a tissue, a biological fluid, a blood sample, a serum sample, a plasma sample, a urine sample, and a skin sample. The biological sample may be a tissue sample that is taken from a tumor in subject who is a patient, taken from a tissue or organ that is suspected of containing cancer cells, or taken from a tissue region adjacent to the tumor or tissue or organ suspected of containing cancer cells. The biological sample may be fresh, or preserved according to standard freezing or tissue fixation protocols using standard cryopreservatives or fixatives, such that the biological tissue sample is frozen, fixed, or paraffin-embedded. The tissue may be for example formalin-fixed, paraffin-embedded (FFPE) tissue.

The method may further comprise obtaining the biological sample from the subject through any typical means, such as by biopsy, swab, needle stick, etc. Expression levels of the miRNA can be determined as described elsewhere herein and in the Examples. The subject may be a patient suspected of having a cancer or at risk for a cancer recurrence. The method may further comprise comparing miRNA expression levels in the biological sample to miRNA expression levels in a normal reference sample, which may be a biological sample from a second human subject or a biological sample taken from the human subject being evaluated. The reference sample is for example a sample believed to be or established to be free or substantially free of cancer cells. When the reference sample is taken from the subject being evaluated, the reference sample may be taken from tissue adjacent to tumor.

The sensitizing miRNAs according to the present disclosure can also be used in a method for determining whether one or more candidate miRNAs increase sensitivity of a subject to treatment with a Bcl-2 family inhibitor. The method can comprise, for example: a) transfecting or reverse transfecting a population of cancer cells with the candidate miRNA or miRNAs; b) contacting the cells with an effective amount of the Bcl-2 family inhibitor, and c) determining the survival rate of the cells, wherein a decrease in cell survival rate is indicative that the miRNA increases sensitivity of the subject to treatment with the Bcl-2 family inhibitor. The population of cells can comprise cells from a mammalian cancer cell line, such as but not limited to HCT-116 cells, CHL1 cells or cells from any of the many known human or mammalian cancer cell lines that are commonly used in cancer research laboratories, such as those maintained at the Sanger Institute (http://www.sanger.ac.uk/genetics/CGP/CellLines/), or the sixty human cancer cell lines maintained at the National Cancer Institute (Frederick, Md.). Transfection of the cells can be achieved using any of a number of widely commercially available transfection reagents sold as suitable for mammalian cancer cell lines, and used according to manufacturer's instructions. Such transfection agents include but are not limited to Lipofectamine or Lipofectamine 2000 (Invitrogen), Arrestin (Open Biosystems), Oligofectamine (Invitrogen), TransIT-TKO (Mirus), and siIMPORTER (Upstate). Reverse transfection can be used for analysis of many miRNAs (or siRNAs) in parallel, and can be achieved using a microarray-based system in which the cells are cultured on a glass slide printed in defined locations with different solutions, each containing a mammalian expression vector containing a different miRNA or siRNA. Alternatively, transfected cell microarrays can be made using a gelatin-based method in which a plasmid is dissolved in an aqueous gelatin solution and printed on a glass slide, for example using mechanical arrayer. The slide is dried and the printed array covered with a suitable lipid-based transfection reagent, which is later removed, the slide placed in a culture dish and covered with cells in medium, leaving the transfected cell microarray to form over about one to two days.

The present disclosure also provides a method for determining whether an miRNA increases sensitivity of a subject to treatment with a Bcl-2 family inhibitor. The method includes a) reverse transfecting a population of cancer cells with the candidate miRNA; b) contacting the cells with an effective amount of the Bcl-2 family inhibitor, and c) determining Mcl-1 expression level in the cells, wherein a decrease in Mcl-1 expression is indicative that the miRNA increases sensitivity of the subject to treatment with the Bcl-2 family inhibitor. Mcl-1 protein expression can be measured using a liquid phase immunoassay using Luminex beads. In brief, an Mcl-1 capture antibody is conjugated to Luminex beads (bead region 9) and an Mcl-1 detection antibody conjugated to biotin. Cells are lysed in a lysis buffer and the lysate incubated with Mcl-1 capture antibody-beads overnight under conditions suitable for specific binding of the capture antibody to the Mcl-1. After washing with cell assay buffer, biotinylated Mcl-1 detection antibody is added and the mixture incubated under conditions suitable for specific binding of detection antibody to the Mcl-1 (e.g., for a period of about 1 h at room temperature). After filtering, streptavidin-phycoerythrin is added and incubated for a time and under conditions suitable for binding to the biotin. Cell assay buffer is added after filtering and the plate is read using a Luminex 200 station. Western blotting can be used to validate the results of the assay.

The sensitizing miRNAs according to the present disclosure can also be used in a method for treating a human subject having or suspected of having a cancer. Sensitizing miRNA's listed in Table 1, for example any one of the miRNAs of SEQ ID NOS. 1-19, including for example oligonucleotides that mimic the activity of those miRNAs, can be used in therapeutic intervention in which the sensitizing miRNAs (or mimics thereof) are delivered to the subject so to promote apoptosis in cancer cells exposed to a Bcl-2 family protein inhibitor, which may result in whole or in part by down-regulating Mcl-1 expression. A "pharmaceutical composition" refers to any chemical or biological compound or composition capable of inducing a desired therapeutic effect when properly administered to a subject, and may include a sensitizing miRNA selected from SEQ ID NOS: 1-27, or in particular from SEQ ID NOS: 1-19, or a mimic thereof (i.e. a synthetic molecule having a sequence selected from SEQ ID NOS: 1-27, or more particularly from SEQ ID NOS: 1-19). A pharmaceutical composition according to the present disclosure is formulated to be compatible with its intended route of administration, and may thus be combined with a pharmaceutically acceptable carrier, diluent or excipient. Routes of administration include parenteral (e.g., intravenous, intradermal, subcutaneous, intraperitoneal, or intramuscular), oral, topical, and transmucosal administration. Solutions or suspensions appropriate for parenteral, intradermal, or subcutaneous application can include, for example, a sterile diluent such as water, saline solution, fixed oils, polyethylene glycols, glycerine, propylene glycol or other synthetic solvents; antibacterial agents such as benzyl alcohol or methyl parabens; antioxidants; buffers; salts or sugars for adjusting tonicity; and acids or bases to adjust pH.

A therapeutically effective amount of an miRNA can be contained in a pharmaceutical composition, wherein a therapeutically effective amount is an amount capable of modulating the sensitivity of a cancer cell to a Bcl-2 family protein inhibitor as may be determined according to methods described elsewhere herein. Factors that may influence the dosage and timing required to effectively treat a subject include the route of administration, growth rate of a tumor, previous treatments, the general health and/or age of the subject, and co-existence of other disorders or diseases. Treatment of a subject with a therapeutically effective amount of a composition can include a single treatment or a series of treatments.

A pharmaceutical composition according to the present disclosure thus may further include a Bcl-2 family protein inhibitor, or a therapy may include co-administration of a sensitizing miRNA such as one selected from SEQ ID NOS: 1-19, or a mimic thereof, together with a Bcl-2 family protein inhibitor. A pharmaceutical composition may include one or more additional chemical compounds, especially one or more cytotoxic compounds, used to treat certain disease such as cancer according to a chemotherapy regimen. Chemotherapeutic agents include alkylating agents, antimetabolites, anthracyclines, plant alkaloids, topoisomerase inhibitors, antitumour agents, tyrosine kinase inhibitors such as imatinib mesylate, and hormonal therapy as known for the treatment of breast cancer. The drugs may be combined in different combinations to form cocktails. A kit including a pharmaceutical composition may include a container holding the pharmaceutical composition together with a delivery device for delivering the composition to the subject. A delivery device may be, for example, a syringe and/or a needle, an aerosol spray device, an atomizer, a dry powder delivery device, or a self-propelling solvent/powder-dispensing device.

As a therapeutic intervention, delivery of the miRNA to a cell or to a subject may be achieved using a delivery vehicle suitable for delivering genetic material, including vehicles such as nucleic acid constructs, vectors, viruses and cells. Nucleic acid constructs can be genetically engineered and may be a non-replicating and linear nucleic acid, a circular expression vector, an autonomously replicating plasmid or viral expression vector. A nucleic acid construct may comprise multiple elements including genes or gene fragments, promoters, enhancers, terminators, poly-A tails, linkers, markers and host homologous sequences for integration. A nucleic acid construct may include for example the sequence of at least one nucleic acid molecule having a sequence selected from Table 1 (SEQ ID NOS: 1-27), and in particular a sequence selected from SEQ ID NOS: 1-19, preceded by a promoter enabling expression of the at least one nucleic acid molecule. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989). A suitable promoter may be selected from the group of constitutive promoters, inducible promoters, organism specific promoters, tissue specific promoters and cell type specific promoters. Examples of promoters include, but are not limited to: constitutive promoters such as: simian virus 40 (SV40) early promoter, a mouse mammary tumour virus promoter, a human immunodeficiency virus long terminal repeat promoter, a Moloney virus promoter, an avian leukaemia virus promoter, an Epstein-Barr virus immediate early promoter, a Rous sarcoma virus (RSV) promoter, a human actin promoter, a human myosin promoter, a human haemoglobin promoter, cytomegalovirus (CMV) promoter and a human muscle creatine promoter, inducible promoters such as: a metallothionine promoter, a glucocorticoid promoter, a progesterone promoter, and a tetracycline promoter, tissue specific promoters such as: HER-2 promoter and PSA associated promoter.

Other delivery vehicles may be used to transport a nucleotide sequence from one medium to another, especially to an intracellular environment. Suitable delivery vehicles include RNA based vehicles, DNA based vehicles/vectors, lipid based vehicles, virally based vehicles and cell based vehicles. Examples of such delivery vehicles include, but are not limited to: biodegradable polymer microspheres, lipid based formulations such as liposome carriers, coating the construct onto colloidal gold particles, lipopolysaccharides, polypeptides, polysaccharides, and viruses including adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector.

A nucleic acid construct as described herein may be included within a recombinant cell, which may be used as a delivery vehicle for the nucleic acid construct, as part of a gene therapy protocol, or in vitro for research purposes. The nucleic acid construct and nucleic acid based vectors can be introduced into cells by techniques well known in the art and including microinjection of DNA into the nucleus of the cell, transfection, electroporation, lipofection/liposome fusion and particle bombardment. Accordingly, a pharmaceutical composition may comprise any of the delivery vehicles described herein, and further comprising any one of SEQ ID NOS: 1-27, especially SEQ ID NOS: 1-19, and in particular any one of SEQ ID NOS: 1-12, and in an exemplary embodiment any one of SEQ ID NOS: 1-10.

The pharmaceutical compositions can be used to treat a subject having or at risk of having cancer. The cancer may be characterized by the overexpression of Mcl-1, and may be caused by the expression or activity of a mutant gene or gene product. Accordingly, the present disclosure includes administration of a composition that includes or mimics the activity of any of the sensitizing miRNA's, such as the miRNAs of SEQ ID NOS: 1-19. The present disclosure contemplates both prophylactic and therapeutic methods of treating a subject having, at risk of or susceptible to a cancer associated with aberrant or unwanted expression or activity of Mcl-1. The treatment may include directly modulating Mcl-1 expression, or Mcl-1 activity for therapeutic purposes. Such treatment involves contacting a cancer cell known or suspected to be resistant to treatment with a Bcl-2 family inhibitor, with a therapeutic agent (e.g. a pharmaceutical composition including an sensitizing miRNA of SEQ ID NOS: 1-19) such that concurrent or later exposure of the cell to a Bcl-2 family protein inhibitor results in an apoptotic response by the cell. Such methods can be performed in vitro (e.g., by culturing the cell with the agent) or, alternatively, in vivo (e.g., by administering the agent to a subject). Such treatment may comprise administering to the subject a therapeutic amount of a Bcl-2 family protein inhibitor and an amount of at least one sensitizing miRNA such as an miRNA selected from the group of SEQ ID NOS: 1-19, or of at least one siRNA of 19-24 bp having a sequence identical to any 19-24 contiguous by of the miRNA, wherein the amount of the at least one miRNA or siRNA is sufficient to sensitize the subject to treatment with the Bcl-2 family protein inhibitor. Sensitization of the cell or subject can be evaluated using any one or more of the functional assays described herein or other assay methods as known in the art.

The sensitizing miRNAs according to the present disclosure can also be used in a method for re-sensitizing a human subject having or suspected of having acquired a resistance to treatment of a cancer with a Bcl-2 family protein inhibitor, the method comprising administering to the subject an amount of at least one sensitizing miRNA such as miRNA selected from the group consisting of SEQ ID NOS: 1-19, or of at least one siRNA of 19-24 bp having a sequence identical to any 19-24 contiguous by of the miRNA, wherein the amount of the at least one miRNA or siRNA is sufficient to re-sensitize the subject to treatment with the Bcl-2 family protein inhibitor. The amount of miRNA or siRNA that is sufficient to re-sensitize the subject to treatment with the Bcl-2 family protein inhibitor will vary according to the delivery method used and the Bcl-2 family protein inhibitor being tested, and can be determined for example by monitoring the subject's response, specifically for example reduction in tumor size, to administration of the Bcl-2 family protein inhibitor following, or together with administration of the miRNA.

The sensitizing miRNAs according to the present disclosure can also be used in a method of promoting apoptosis in a cell comprising decreasing the expression of Mcl-1 in the cell by contacting the cell with an amount of at least one miRNA selected from the group consisting of SEQ ID NOS: 1-12, or of at least one siRNA of 19-24 bp having a sequence identical to any 19-24 contiguous by of the miRNA, or a combination thereof, wherein the amount of the at least one miRNA or siRNA is sufficient to decrease the activity of Mcl-1 in the subject. In an exemplary embodiment of the method, the one or more miRNAs are selected from the group consisting of SEQ ID NOS: 1-10. The amount of miRNA or siRNA that is sufficient will vary according to the delivery method and vehicle used and can be readily determined using the Mcl-1 protein expression assay as described above.

Kits

The sensitizing miRNAs according to the present disclosure also provide the basis for a kit useful for assaying miRNA expression levels in a biological sample of a subject. The kit may comprise: a) a panel of two or more oligonucleotide primers or probes, each primer or probe capable of selectively binding a human miRNA selected from Table 1, such as an miRNA selected from SEQ ID NOS: 1-19; b) one or more reagents for amplifying the miRNA present in the biological sample using the primers or probes; and c) instructions for quantifying expression levels of the miRNA in the biological sample and evaluating the sensitivity of the subject to treatment with a Bcl-2 family protein inhibitor based on the expression levels of the miRNA. In an exemplary embodiment of the kit, the one or more miRNAs are selected from the group consisting of SEQ ID NOS: 1-12. In another exemplary embodiment of the kit, the one or more miRNAs are selected from the group consisting of SEQ ID NOS: 1-10. The kit may comprise any detection material or device such as a labeling system, a cocktail of components such as solutions or suspensions required for any type of PCR, especially real-time quantitative RT-PCR. The kit may comprise a solid support, wherein the oligonucleotides such as probes are immobilized on the solid support. The solid support may comprise one or more components selected from the group consisting of: a membrane, a chip, a disk, a strip, a filter, a microsphere, a slide, a multiwell plate, a bead, or an optical fiber. The kit may further comprise a tool such as a cotton swab, cup or needle and syringe for obtaining the biological sample, or a container for storing the biological sample, or both, or the tool and the container may be the same item, for example a cup for receiving and storing a urine sample. In the kit, the biological sample may be selected from the group consisting of: a cell lysate, a cell culture, a cell line, a tissue, a biological fluid, a blood sample, a serum sample, a plasma sample, a urine sample, and a skin sample. The one or more reagents may comprise one or more miRNA hybridization or amplification reagents for any two or more of the miRNAs, including for example a DNA polymerase and appropriate buffer solutions. Test kits according to the present disclosure preferably include instructions for carrying out one or more of the presently disclosed methods. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

C. Adaptations of the Methods of the Present Disclosure

One skilled in the art would readily appreciate that the oligonucleotides, methods, kits and related compositions described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by exemplary embodiments and optional features, modification and variation of the concepts herein disclosed may be resorted to by those skilled in the art, and that such modifications and variations are considered to be within the scope of this invention as defined by the appended claims.

EXAMPLES

By way of example, and not of limitation, examples of the present disclosures shall now be given.

For the following examples, materials and methods were as follows: ABT-263 was synthesized at Abbott Laboratories (Abbott Park, Ill.). All siRNAs and miRNAs were purchased from Dharmacon (Lafayette, Colo.).

Example 1

Cell Culture, Transfection, and Cell-Based Assays

HCT-116 and CHL1 cells were purchased from the American Type Culture Collection (ATCC) and cultured in DMEM (Invitrogen Corp., Grand Island, N.Y.) supplemented with 10% fetal bovine serum (Invitrogen) and 1% penicillin/streptomycin (Invitrogen). All cell lines were maintained in a humidified chamber at 37° C. containing 5% CO2. These cells were authenticated by morphological, cell proliferation and Mycoplasma tests recommended in the ATCC Technical Bulletin no, 8 (2007). Cells were reverse transfected at 1.5–2.5×10^4 cells/100 ml in 96-well tissue culture plates. siRNA or miRNA transfection was performed using Lipofectamine 2000 according to manufacturer's instructions (Invitrogen). For Mcl-1 and Bcl-xl siRNA transfections, a final concentration of 12.5 nM siRNA was used. For miRNA transfections, a final concentration of 50 nM miRNA was used. The cells were then grown in medium without antibiotic for 2 days before harvesting. For reporter experiments, 100 ng of pcDNA3-Mcl-1-3'UTR-luciferase reporter construct (21) was included in the liposome complex mix. Forty-eight hours after transfection, cells were assayed for viability using CellTiter Glo Luminescent cell viability assay according to the manufacturer's protocol (Promega). Caspase 3/7 activity was measured using the Caspase-Glo 3/7 assay (Promega). Luciferase activity was measured using the Steady-Glo reagent according to the manufacturer's protocol (Promega).

Example 2

MiRNA Mimic Library Screen and Data Analysis

Figure 1B:
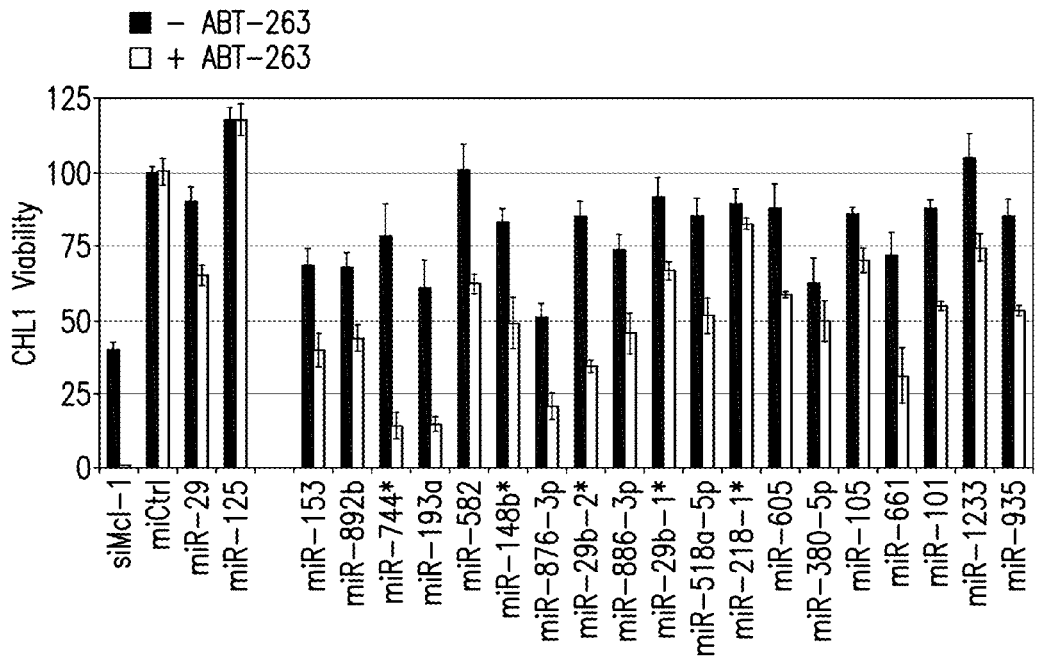
FIG. 1B is a bar graph showing results of a Bcl-2 inhibitor sensitization screen of an miRNA library, showing modulation of CHL1 cell sensitivity to ABT-263 in cells transfected with sensitizing miRNA.
Figure 1C:
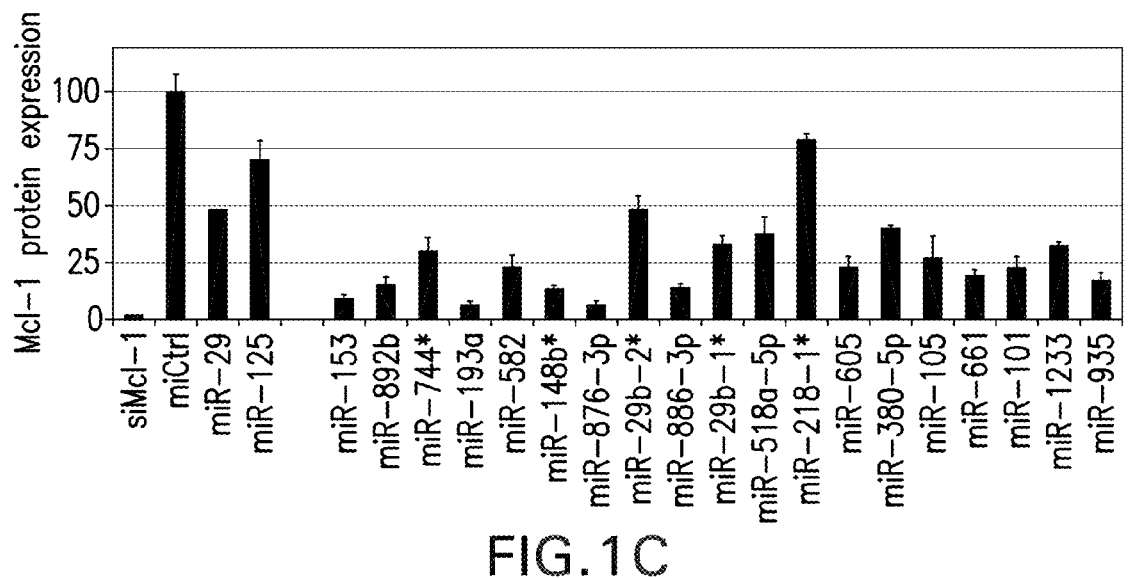
FIG. 1C is a bar graph showing modulation of Mcl-1 protein expression in CHL1 cells, by sensitizing miRNAs.

HCT-116 cells were reverse transfected as described in Example 1 above. Three replica plates were treated with 1 µM ABT-263 in media. After 48 h, the cell viability was assessed using the CellTiter-Glo assay, as shown in FIG. 1. FIG. 1A shows miRNAs that sensitize HCT-116 cells to ABT-263. HCT-116 cells were reverse transfected with sensitizing miRNAs in the presence or absence of 1 µM ABT-263 for 48 hours. Cell viability was measured with CellTiter Glo assay. MiR-29 and miR-125 were used as positive and negative controls for this assay. miRNAs that sensitize HCT-116 cells to ABT-263 by more than 25% are shown. FIG. 1B is a bar graph showing miRNAs that sensitize CHL1 cells to ABT-263. CHL1 cells were reverse transfected with sensitizing miRNAs in the presence or absence of 1 µM ABT-263 for 48 hours. Cell viability was measured with CellTiter Glo assay. Only miRNAs that sensitize HCT-116 cells to ABT-263 by more than 25% were shown. (See FIG. 6 for the complete list of 42 miRNAs). FIG. 1C is a bar graph showing modulation of Mcl-1 protein expression by sensitizing miRNAs in CHL1 cells. CHL1 cells were reverse transfected with sensitizing miRNAs. Mcl-1 expression was measured using a Luminex-based assay as described in the Methods section.

Example 3

Quality Control of the MiRNA Mimic Library Screen

Quality of the miRNA screen was evaluated as follows. To determine the dynamic range of the miRNA screen, the Z factor was calculated. In brief, $Z=(x-m)/s$ where x is the raw data point to be standardized, s is the standard deviation of the mimics population, and m is the mean of the mimics population. Using a Z score cutoff of less than −1.5, 80 miRNAs were identified, which either have effects on the cell survival by themselves or sensitize cells to Bcl-2 inhibitor. After subtracting miRNAs previously identified to be toxic by themselves (Z←1.5) and mimic repeats from our hits, 42 miRNAs were identified, which modulate the sensitivity to Bcl-2 inhibitor (with a Z score difference of at least 0.8 between treatment and no treatment). These miRNAs were further evaluated in the presence or absence of 1 µM ABT-263 in HCT-116 and CHL1 cells. Using a cutoff of 25% sensitization to ABT-263 treatment, 19 and 17 miRNAs were confirmed to sensitize HCT-116 and CHL1 cells to ABT-263, respectively. FIG. 5A shows a scatter plot of averaged Z-scores from the ABT-263 sensitization screen carried out in triplicate with ABT-263. FIG. 5B shows reproducibility of screen using correlation of ABT-263 sensitivity Z-scores of the three replicates of the screen. Spearman correlation coefficient r=0.85, 0.8, and 0.82 for 1 vs. 2, 1 vs. 3, and 2 vs. 3 respectively. FIG. 5C shows the percentage of surviving HCT-116 cells for control, Mcl-1, and Bcl-xl siRNA transfections used as controls in the screens. Each bar represents the survival percentage for each siRNA from one plate. FIG. 5D shows the percentage of surviving HCT-116 cells for miControl, miR-29, miR-125, miR-153, and miR-193 transfections used as controls in the screens. Each bar represents the mean survival percentage for each miRNA from 10 plates.

Example 4

Protein Assays

Figure 6A:
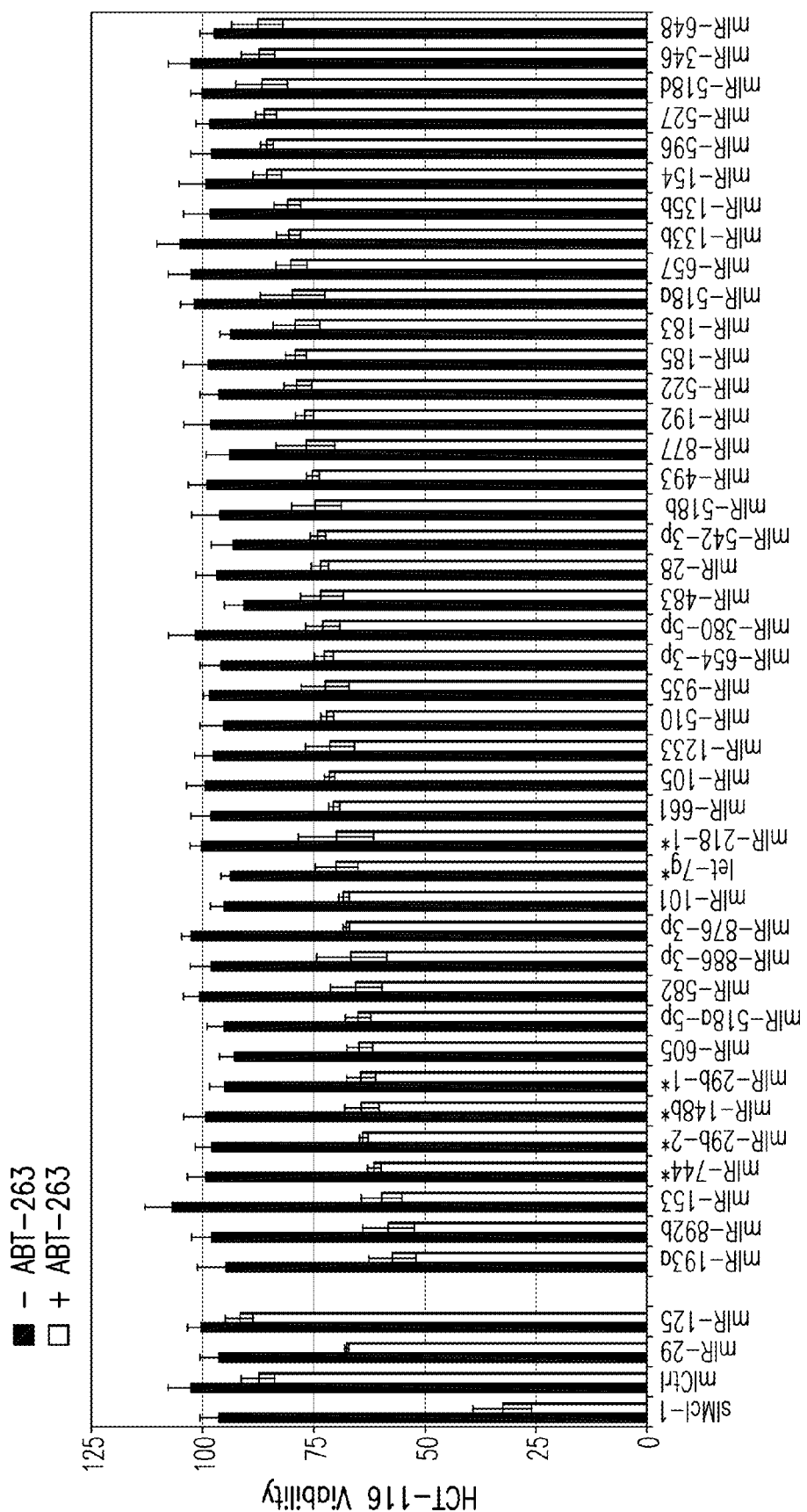
FIG. 6A shows results of a Bcl-2 inhibitor sensitization screen of an miRNA library in HCT-116 cells reverse transfected with miRNA in the presence or absence of ABT-263.
Figure 6B:
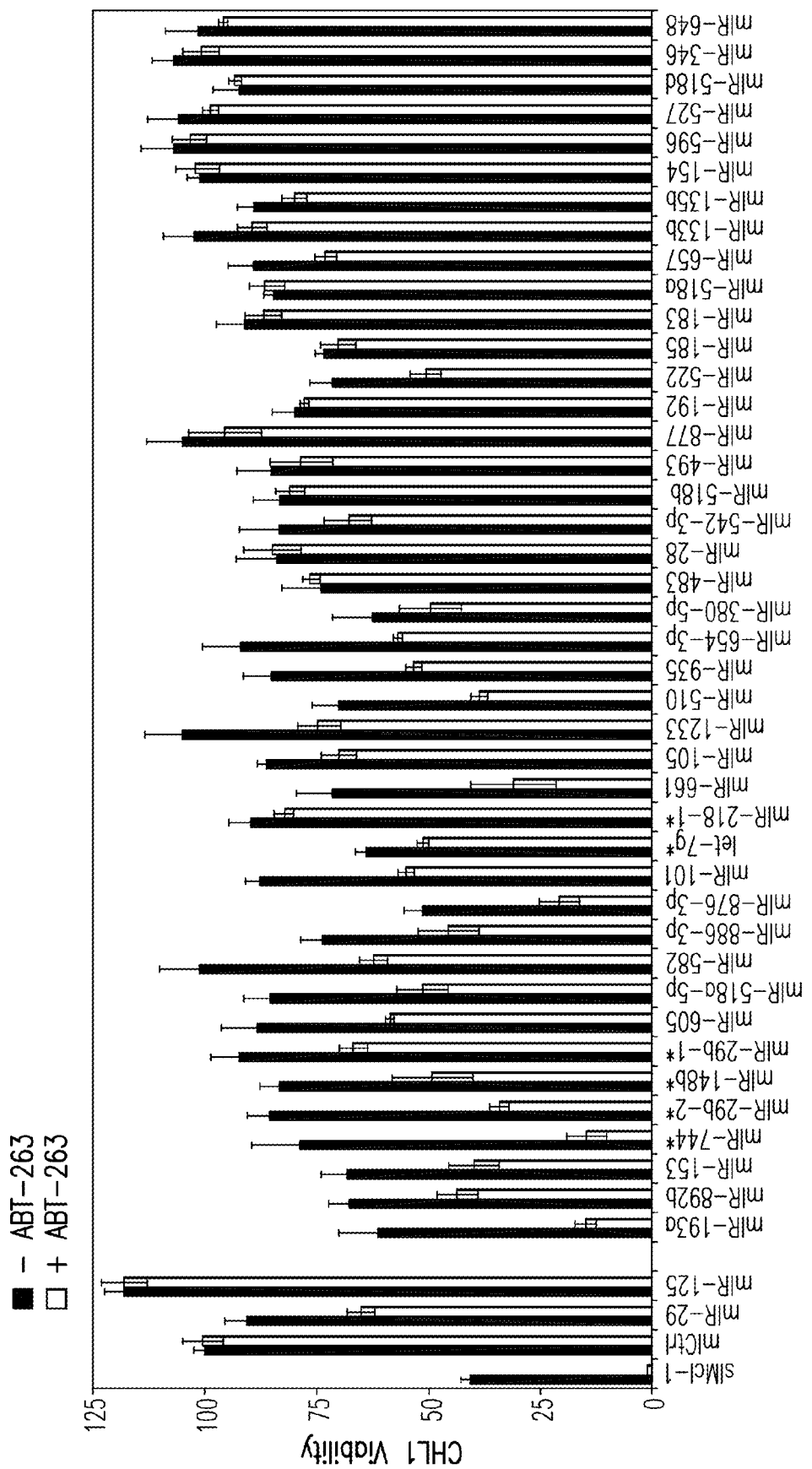
FIG. 6B shows results of a Bcl-2 inhibitor sensitization screen of an miRNA library in CHL1 cells reverse transfected with miRNA in the presence or absence of ABT-263.
Figure 6C:
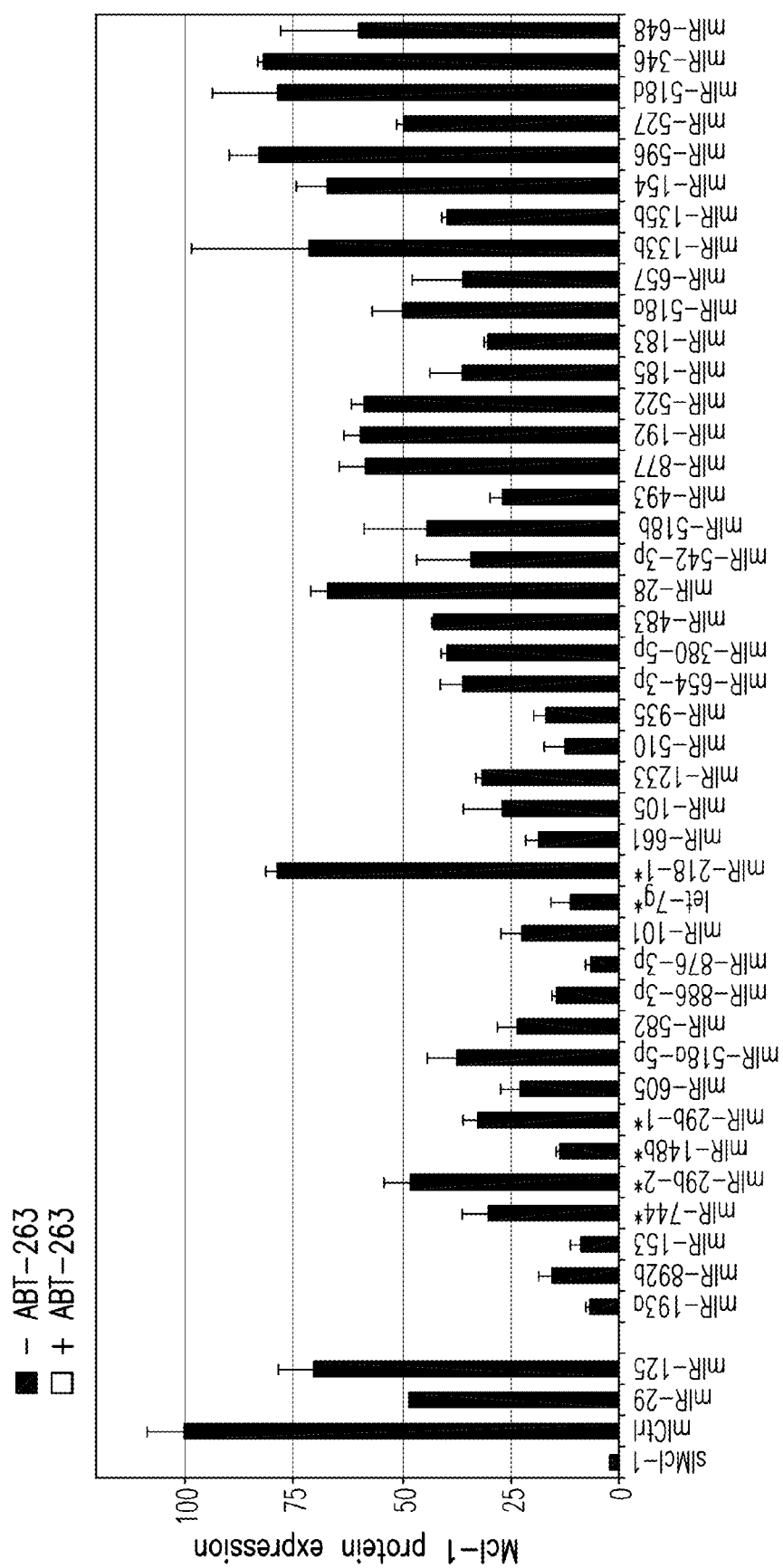
FIG. 6C shows modulation of Mcl-1 protein expression by sensitizing miRNAs in CHL1 cells.
Figure 6D:
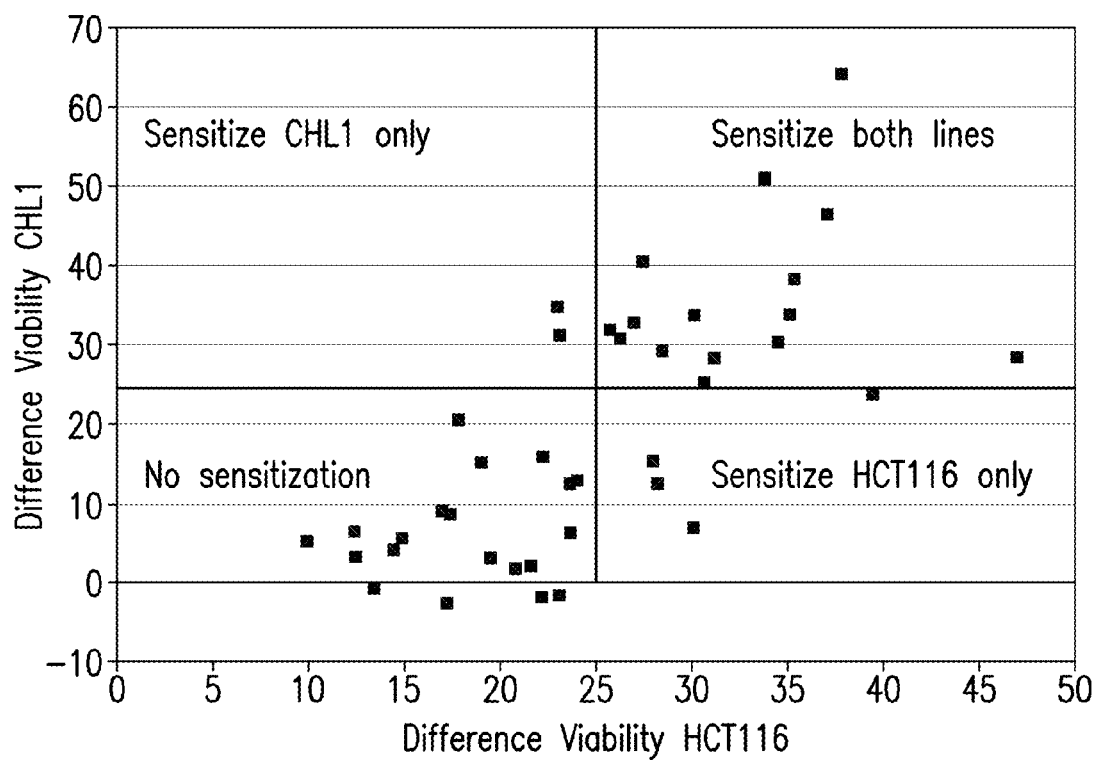
FIG. 6D is a scatter plot of miRNAs that sensitize HCT-116, CHL1, both cell lines, or neither.
Figure 6E:
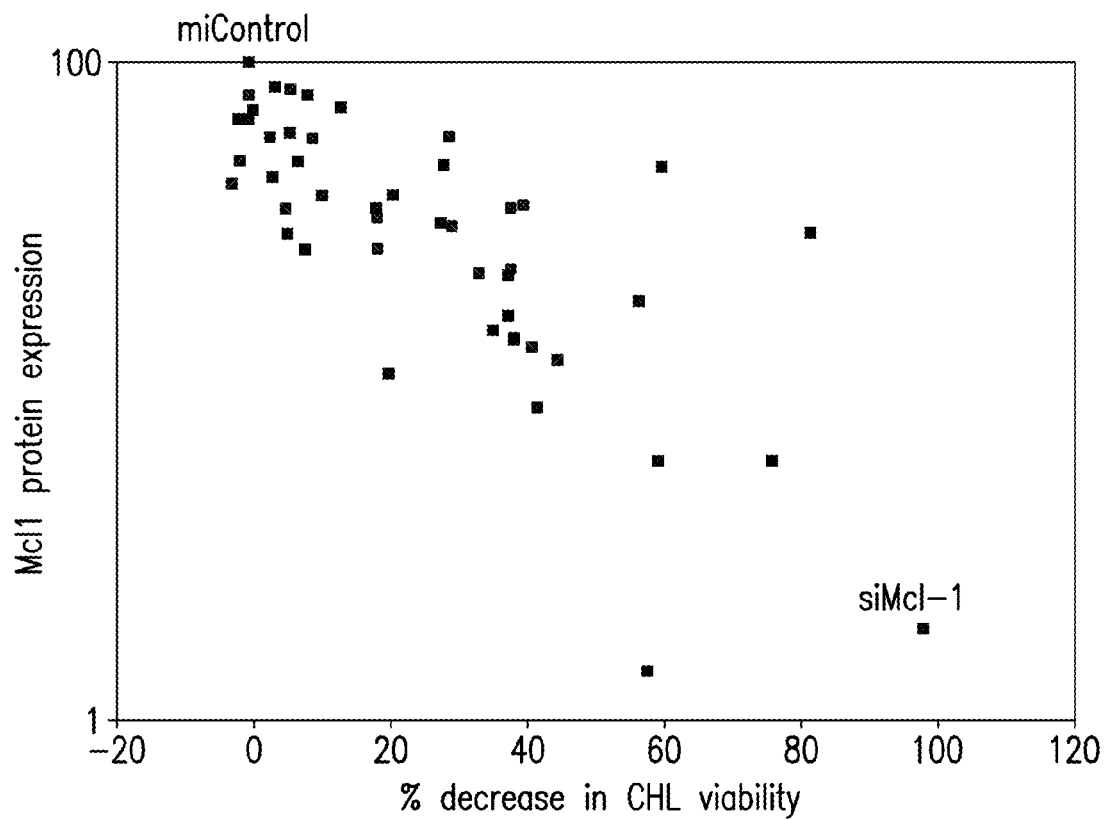
FIG. 6E is a plot of the correlation between the levels of sensitization to ABT-263 by miRNAs and the levels of Mcl-1 protein knockdown in CHL1 cells.
Figure 7:
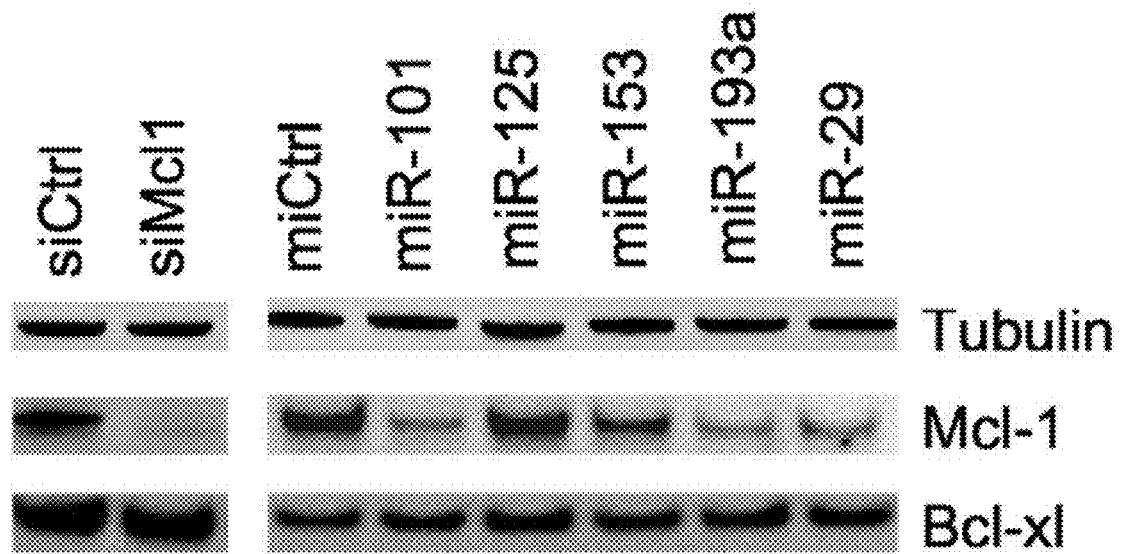
FIG. 7 shows Western blots of Mcl-1 and Bcl-xl protein in HCT-116 cells treated with control or Mcl-1 siRNA and control or Mcl-1 targeting miRNAs.

Mcl-1 protein expression was measured using a new Mcl-1 assay based on the Luminex technology. In brief, an Mcl-1 capture antibody (Santa Cruz) was conjugated to Luminex beads (bead region 9) and an Mcl-1 detection antibody (Santa Cruz) was conjugated to biotin (Linco). Cells were lysed in a lysis buffer (Millipore), and the lysate was incubated with Mcl-1 capture antibody-beads overnight at 4° C. with shaking in a cell assay buffer (Millipore). After washing with cell assay buffer twice, a biotinylated Mcl-1 detection antibody was added and incubated for 1 h at room temperature with shaking. After filtering, streptavidin-phycoerythrin (Millipore) was added and incubated for 30 min at room temperature with shaking. Cell assay buffer was added after filtering and the plate was read using a Luminex 200 station. The liquid-phase quantitative protein assay was used to measure the levels of Mcl-1 in cells. Western blotting was used to validate the assay with Mcl-1 siRNA and five predicted Mcl-1-targeting miRNAs (FIG. 7). Using this new Mcl-1 quantitative assay, the effect of these miRNAs on the Mcl-1 protein levels in CHL1 cells was measured. All the sensitizing miR-NAs potently silenced Mcl-1 expression (FIG. 1C and FIG. 6C). The levels of sensitization to ABT-263 correlate with the levels of Mcl-1 protein knockdown (FIG. 6E). Taken together, these results indicate that the sensitizing miRNAs identified in the functional screen are important modulators of Mcl-1 expression, which determine the sensitivity of different cancer cells to Bcl-2 family inhibitors.

Example 5

Testing of Predicted Modulators of Mcl-1

Figure 4:
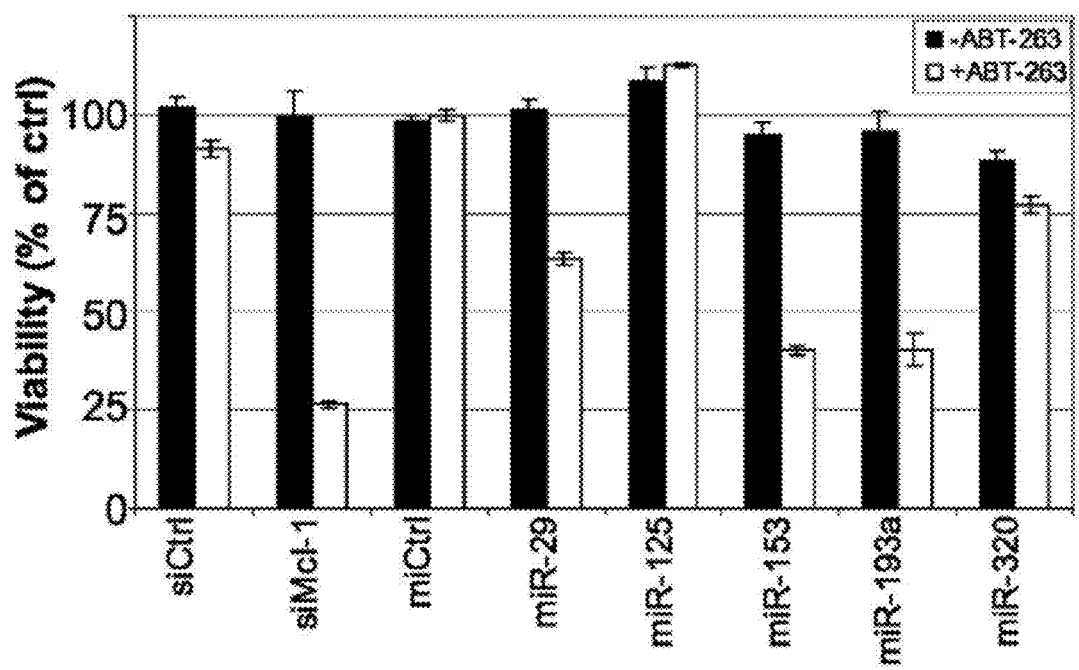
FIG. 4 is a bar graph of cell viability after 48 hours of HCT-116 cells reverse transfected with Mcl-1 siRNA and predicted Mcl-1 targeting miRNAs, and treated with ABT-263.

To identify miRNAs that modulate sensitivity of cells to Bcl-2 family inhibitor ABT-263, an miRNA "sensitization" screen was performed using an miRNA mimic library in the presence of ABT-263. The screen was conducted in a colon cancer cell line HCT-116. The screen was optimized so that (i) transfection of HCT-116 with the control siRNAs and miRNAs would not be toxic; (ii) ABT-263 alone would not affect the cell viability by more than 25% in the presence of the control siRNA and miRNA; (iii) transfection of HCT-116 cells with Mcl-1 siRNA would not affect cell viability, but significantly sensitize cells to ABT-263 (FIG. 4). In addition, miRNAs that were predicted in silico to target Mcl-1 (miR-29, miR-125, miR-153, miR-193a, and miR-320) (4) were evaluated for ability to modulate the sensitivity of HCT-116 cells to Bcl-2 inhibitor. Synthetic miRNA mimics were reverse transfected into HCT-116 cells in the presence or absence of ABT-263 (FIG. 4). Reverse transfection of Mcl-1 siRNA and predicted Mcl-1-targeting miRNAs sensitized HCT-116 cells to 1 µM ABT-263 after 48 hours. Transfection of miR-153 and miR-193a sensitized the cells to the Bcl-2 inhibitor by ~50%, but the effect of miR-29 and miR-320 was much weaker. miR-125 did not sensitize HCT-116 cells to ABT-263 although predicted in silico to do so. These results indicate that miRNAs modulate sensitivity of cancer cells to Bcl-2 inhibitors, and also pointed at limitations of the in silico prediction of miRNA targets.

Example 6

MiRNA Sensitization Screen

HCT-116 cells were reverse transfected with a library of 810 annotated miRNA mimics in triplicate in the presence of 1 µM ABT-263 (FIG. 5A). Viability of cells was determined after 2 days. Comparison of the three replicates suggests high reproducibility of the screen (FIG. 5B). Both siRNA and miRNAs targeting Mcl-1 significantly sensitized the cells to the Bcl-2 inhibitor (FIGS. 5C and 5D), indicating high sensitivity of the screen. Z-scores were used to select candidate miRNAs for subsequent experiments. Of 810 miRNA mimics, 80 increased cell death in the presence of ABT-263. Thirty-eight of these 80 miRNAs either reduced cell viability in the absence of ABT-263 (Z←1.5) or represented mimic replicates from the screen, and therefore were not subjected to further testing. The remaining 42 miRNAs were tested in a secondary screen to assess their effect in the presence or absence of ABT-263. MiR-29 and miR-125 were used as control for this screen. Nineteen of them sensitized HCT-116 cells to ABT-263 by greater than 25% without significantly reducing the viability of the cells in the absence of the drug (FIG. 1A and FIG. 6A). FIGS. 6 A-E shows the results of further screening. FIG. 6A identifies miRNAs that sensitize HCT-116 cells to ABT-263. HCT-116 cells were reverse transfected with sensitizing miRNAs in the presence or absence of 1 µM ABT-263 for 48 hours. Cell viability was measured with CellTiter Glo assay. MiR-29 and miR-125 were used as positive and negative controls for this assay. FIG. 6B identifies miRNAs that sensitize CHL1 cells to ABT-263. CHL1 cells were reverse transfected with sensitizing miRNAs in the presence or absence of 1 µM ABT-263 for 48 hours. Cell viability was measured with CellTiter Glo assay. FIG. 6C shows modulation of Mcl-1 protein expression by sensitizing miRNAs in CHL1 cells. CHL1 cells were reverse transfected with sensitizing miRNAs. Mcl-1 expression was measured using Luminex assay as described in the Methods section. FIG. 6D identifies miRNAs that sensitize HCT-116, CHL1, both cell lines, or neither. FIG. 6E shows that the levels of sensitization to ABT-263 by miRNAs correlate with the levels of Mcl-1 protein knockdown in CHL1 cells.

Profiles of miRNA expression vary among cancer cell lines and normal tissues, possibly resulting in differences in the effects of the same mimic on different lines. A panel of the 42 miRNAs was tested in CHL-1 melanoma cells. Seventeen out of 42 of these miRNAs sensitized CHL1 cells to ABT-263 by greater than 25% (FIG. 1B and FIG. 6B). It should be noted that silencing Mcl-1 in the absence of ABT-263 affected CHL1 cell viability, because CHL1 cells partially depend on Mcl-1 for survival as shown by Mcl-1 siRNA (FIG. 1B). Fifteen of these miRNAs overlapped with the hits from HCT-116 cells (FIG. 6D), confirming the sensitization effect of these miRNAs.

Example 7

Sensitizing MiRNAs Induce Caspase 3/7 Activity in the Presence of ABT-263

Figure 2:
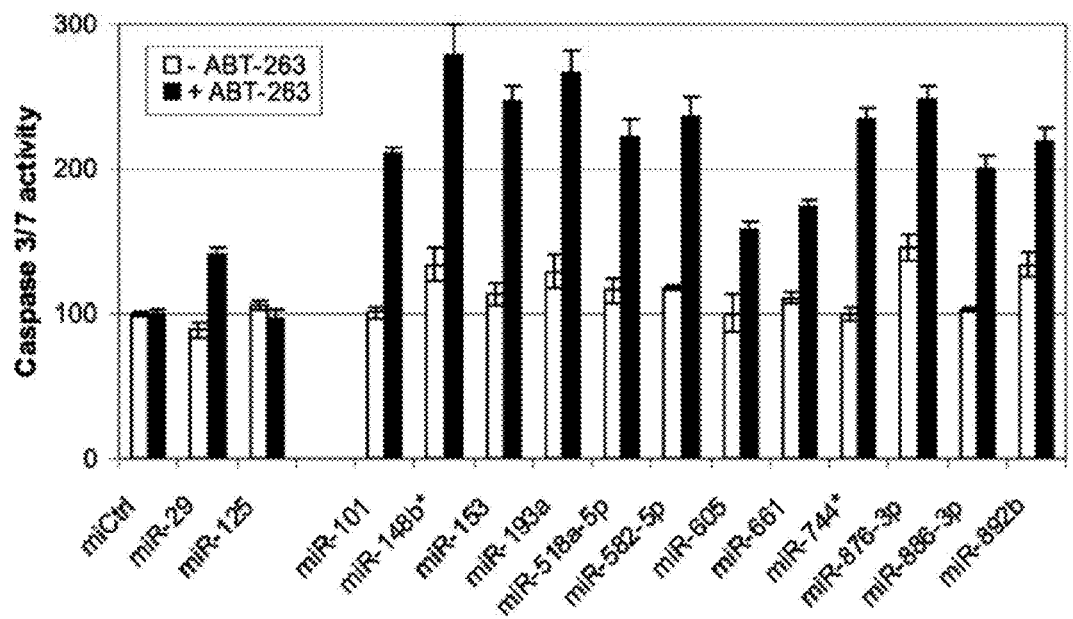
FIG. 2 is a bar graph showing the effect on caspase 3/7 activity of sensitizing miRNAs in HCT-116 cells that were reverse transfected with sensitizing miRNAs in the presence or absence of 1 µM ABT-263.

To determine if the sensitizing miRNAs induce apoptosis, HCT-116 cells were transfected with the twelve most potently sensitizing miRNAs (in both HCT-116 and CHL1 cells) and caspase 3/7 activity measured in the presence or absence of ABT-263. MiR-29 and miR-125 were used as positive and negative controls. More specifically, HCT-116 cells were reverse transfected with sensitizing miRNAs in the presence or absence of 1 µM ABT-263. Caspase 3/7 activity was measured after 24 hours. MiR-29 and miR-125 were used as positive and negative controls for this assay. Data is presented in FIG. 2 as % of control after normalization to control miRNA. As shown in FIG. 2, all the sensitizing miRNAs had a significant increase in caspase 3/7 activity in the presence of ABT-263. The results indicate that the sensitizing miRNAs restore the ability of ABT-263-resistant cells to undergo apoptosis.

Example 8

Mcl-1 is the Direct Target of Most of the Bcl-2 Inhibitor-Sensitizing MiRNAs

Figure 3:
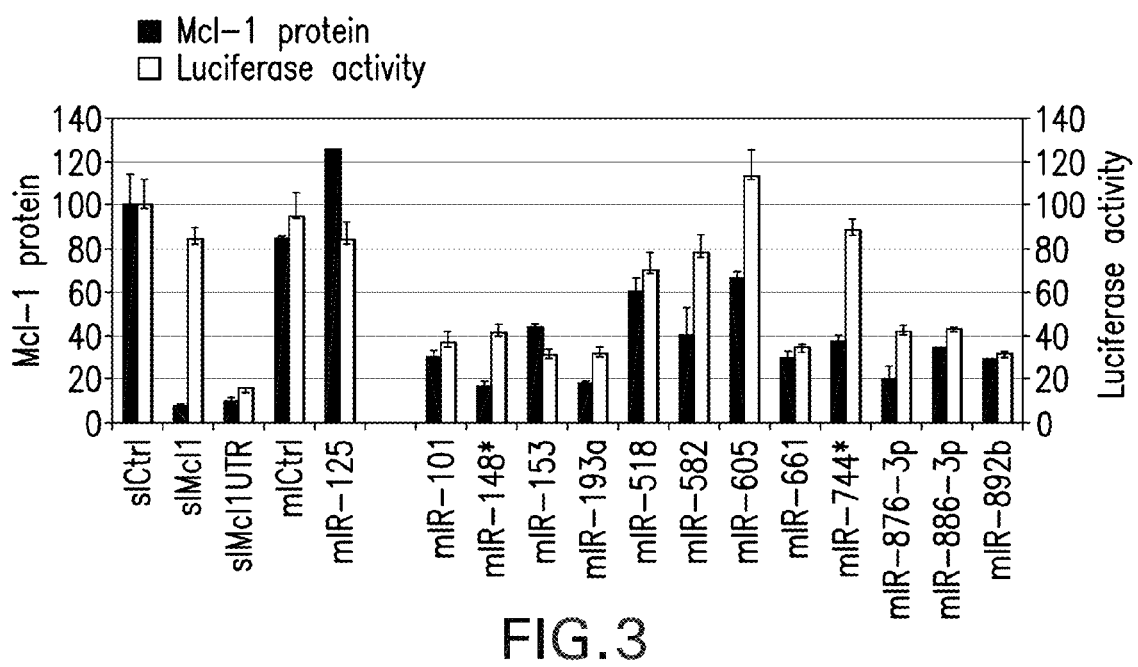
FIG. 3 is a bar graph of normalized Mcl-1 protein expression in HCT-116 cells cotransfected with Mcl-1 UTR reporter and Mcl-1 siRNAs or sensitizing miRNAs.

MiRNA could modulate sensitivity to ABT-263 through several mechanisms: by directly targeting the Mcl-1 gene 3'-UTR and repressing protein translation or by targeting molecules involved in regulating Mcl-1 expression or function. In addition, some miRNAs may modulate ABT-263 sensitivity in an Mcl-1-independent fashion. Measure was taken of the effect of two Mcl-1 siRNAs and the twelve strongest sensitizing miRNAs on the Mcl-1 protein levels in HCT-116 cells using the Mcl-1 quantitative assay described above. HCT-116 cells were cotransfected with 100 ng Mcl-1 UTR reporter and Mcl-1 siRNAs or sensitizing miRNAs (50 nM) for 48 hours. Mcl-1 protein expression was measured using the Mcl-1 Luminex assay. Luciferase activity was measured using Steady Glo reagent. In FIG. 3, data is presented as % of control after normalization to control siRNA. MiR-125 was used as a negative control for this assay. As shown in FIG. 3, two siRNAs targeting either the open reading frame (ORF) or 3'-UTR of Mcl-1 strongly knocked down the expression of Mcl-1 in HCT-116 cells. All the sensitizing miRNAs decreased the expression of Mcl-1 (FIG. 3), indicating that the sensitization of cells to ABT-263 was due to the modulation of Mcl-1 expression.

Figure 8:
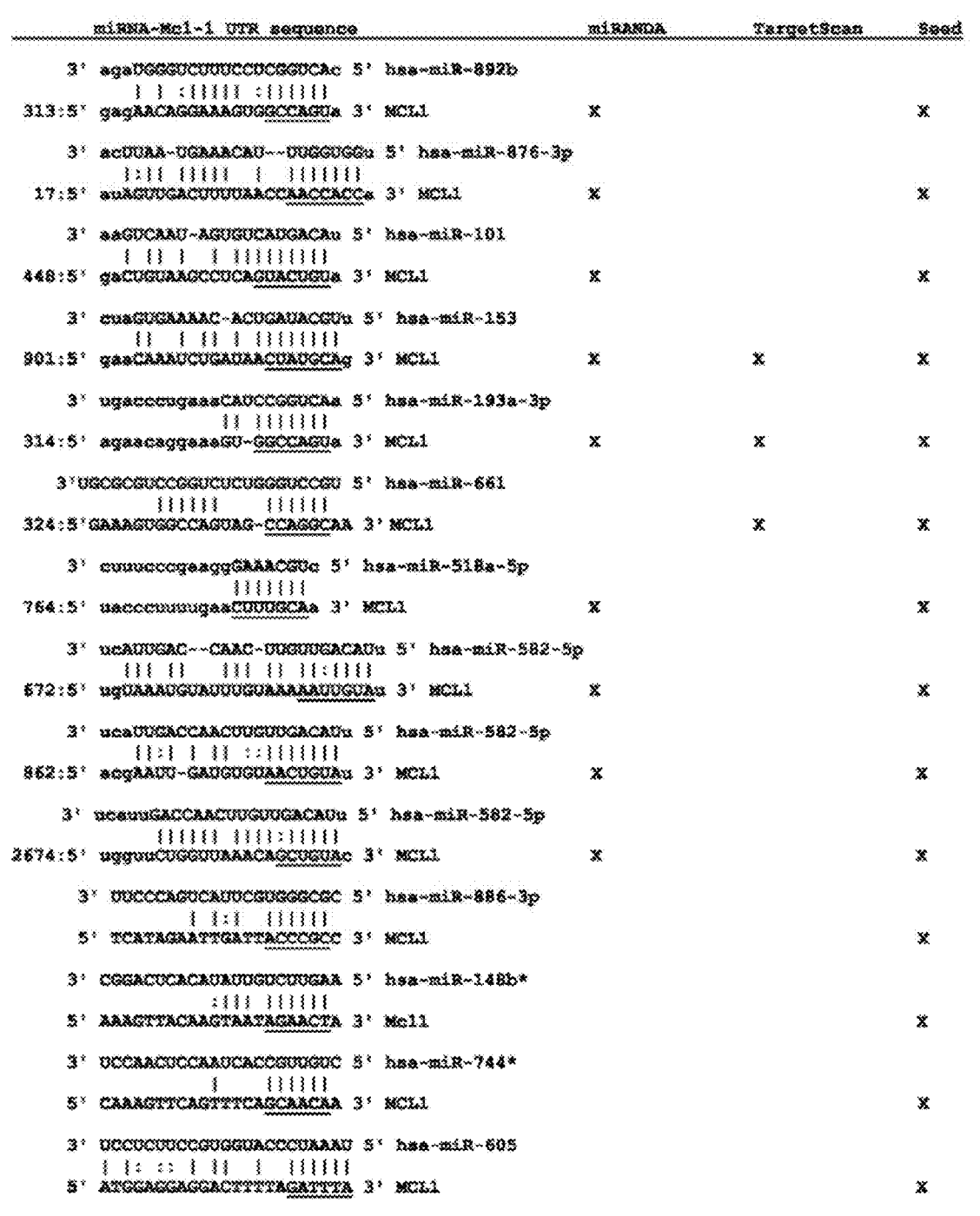

To determine whether the effect of these strongest sensitizing miRNAs on the Mcl-1 gene was direct, two approaches were used: (1) in silico prediction of binding to the 3'-UTR of Mcl-1 and (2) an Mcl-1 3'-UTR reporter assay to determine if the miRNA affects protein expression directly. The binding of miRNA to its target is determined by multiple factors, including the seed sequence and favorable thermodynamic hybridization (7, 11, 12). Therefore, the seed sequence of miRNA hits binding to the 3'-UTR of Mcl-1 was found using two prediction algorithms, TargetScan (16) and miRANDA (22, 23), or by seed sequence analysis. TargetScan and miRANDA predicted that 3 miRNAs (miR-661, miR-153 and miR-193a) and 7 miRNAs (miR-892b, miR876-3p, miR-101, miR-518a-5p, miR582-5p, miR-153 and miR-193a) can bind to the 3'-UTR of Mcl-1, respectively (FIG. 8). In FIG. 8, the seed sequence of miRNA binding to Mcl-1 3'-UTR sequence is underlined. Only two miRNAs (miR-153 and miR-193a) are predicted by both algorithms. Interestingly, the binding sites of the remaining four miRNAs (miR-886-3p, miR-148*, miR-744*, and miR-605) were found using seed sequence analysis.

To test if these miRNAs bind to Mcl-1 3'-UTR directly, a reporter assay was developed in which ~1 kb of the Mcl-1 3'-UTR immediately adjacent to the ORF was subcloned downstream of a luciferase reporter in a pcDNA3 vector. Potential binding sites of the test mimics within this 1 kb of the Mcl-1 3'-UTR are shown in FIG. 8. The specificity of the reporter assay was first evaluated by the cotransfection of the Mcl-1 siRNAs targeting either the ORF or 3'-UTR regions and the reporter construct in HCT-116 cells. Although both siRNAs substantially reduced the protein levels of Mcl-1, only the siRNA targeting the 3'-UTR strongly reduced the luciferase activity (FIG. 3). Next, the twelve strongest sensitizing miRNA mimics and the Mcl-1 3'-UTR-luciferase reporter construct were cotransfected into HCT-116 cells. After two days, the luciferase activity was measured. All the mimics that potently knocked down Mcl-1 expression, except miR-605 and miR-744*, substantially reduced the luciferase activity (FIG. 3). Both miR-605 and miR-744* affected the Mcl-1 protein expression but did not reduce the luciferase activity, indicating that these miRNAs regulate the expression of a modulator of Mcl-1 protein or pathway.

Example 9

Lower Expression of Sensitizing MiRNAs in Tumors Compared with Normal Tissues

Figure 9:
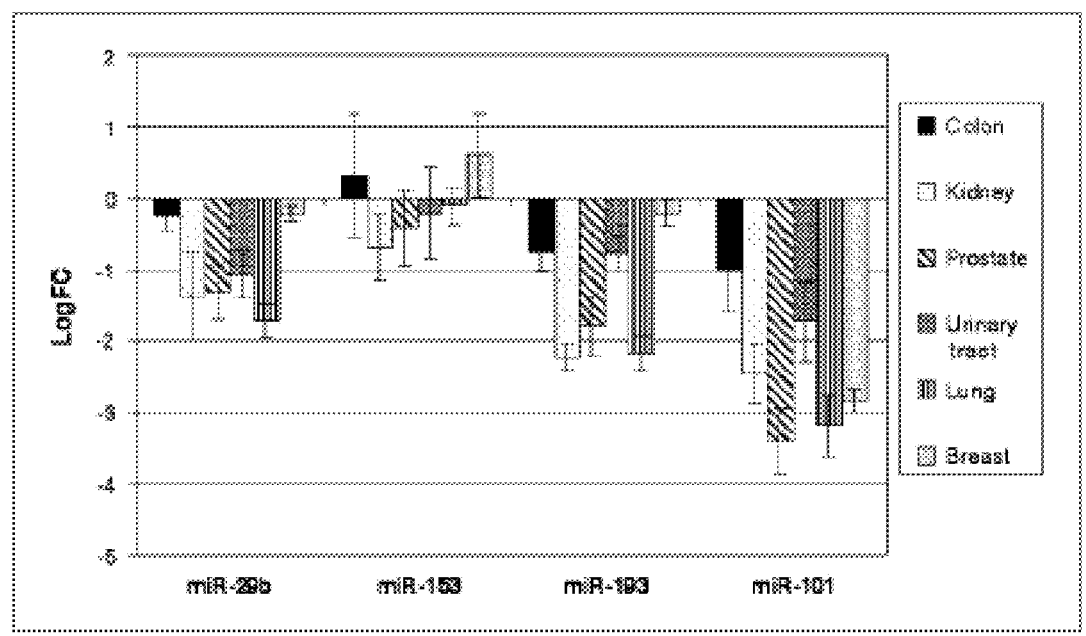
FIG. 9 is a bar graph showing lower expression of four sensitizing miRNAs in tumors as compared to normal tissue.

To evaluate the potential role of the sensitizing miRNAs in cancer, their expression in tumors was compared to that in normal tissue using an existing miRNA expression database (8). The expression of four miRNAs was available. The expression of each miRNA was median centered across all tissues, and expression of each miRNA was the averaged for the tissue subgroup. The log fold change of expression between tumors versus normal tissue was plotted as a bar graph (FIG. 9), showing that expression of these miRNAs is much lower in six tumor types than in normal tissue. Bars indicate standard deviation.

REFERENCES

1. Oltersdorf T, Elmore S W, Shoemaker A R, et al. An inhibitor of Bcl-2 family proteins induces regression of solid tumours. Nature 2005; 435(7042):677-81.
2. Tahir S K, Yang X, Anderson M G, et al. Influence of Bcl-2 family members on the cellular response of small-cell lung cancer cell lines to ABT-737. Cancer Res 2007; 67(3):1176-83.
3. Craig R W. MCL1 provides a window on the role of the BCL2 family in cell proliferation, differentiation and tumorigenesis. Leukemia 2002; 16(4):444-54.
4. Mott J L, Kobayashi S, Bronk S F, Gores G J. mir-29 regulates Mcl-1 protein expression and apoptosis. Oncogene 2007; 26(42):6133-40.
5. Su H, Yang J R, Xu T, et al. MicroRNA-101, down-regulated in hepatocellular carcinoma, promotes apoptosis and suppresses tumorigenicity. Cancer Res 2009; 69(3):1135-42.
6. Crawford M, Batte K, Yu L, et al. MicroRNA 133B targets pro-survival molecules MCL-1 and BCL2L2 in lung cancer. Biochem Biophys Res Commun 2009; 388(3):483-9.
7. Bartel D P. MicroRNAs: target recognition and regulatory functions. Cell 2009; 136(2):215-33.
8. Lu J, Getz G, Miska E A, et al. MicroRNA expression profiles classify human cancers. Nature 2005; 435(7043):834-8.
9. Lim L P, Lau N C, Garrett-Engele P, et al. Microarray analysis shows that some microRNAs downregulate large numbers of target mRNAs. Nature 2005; 433(7027):769-73.
10. Farh K K, Grimson A, Jan C, et al. The widespread impact of mammalian MicroRNAs on mRNA repression and evolution. Science 2005; 310(5755):1817-21.
11. Sethupathy P, Megraw M, Hatzigeorgiou A G. A guide through present computational approaches for the identification of mammalian microRNA targets. Nat Methods 2006; 3(11):881-6.
12. Mendes N D, Freitas A T, Sagot M F. Current tools for the identification of miRNA genes and their targets. Nucleic Acids Res 2009; 37(8):2419-33.
13. Lewis B P, Burge C B, Bartel D P. Conserved seed pairing, often flanked by adenosines, indicates that thousands of human genes are microRNA targets. Cell 2005; 120(1):15-20.
14. Lewis B P, Shih I H, Jones-Rhoades M W, Bartel D P, Burge C B. Prediction of mammalian microRNA targets. Cell 2003; 115(7):787-98.
15. Rehmsmeier M, Steffen P, Hochsmann M, Giegerich R. Fast and effective prediction of microRNA/target duplexes. Rna 2004; 10(10):1507-17.
16. Grimson A, Farh K K, Johnston W K, Garrett-Engele P, Lim L P, Bartel D P. MicroRNA targeting specificity in mammals: determinants beyond seed pairing. Mol Cell 2007; 27(1):91-105.
17. Cheng C, Li L M. Inferring microRNA activities by combining gene expression with microRNA target prediction. PLoS One 2008; 3(4):e1989.
18. Robins H, Li Y, Padgett R W. Incorporating structure to predict microRNA targets. Proc Natl Acad Sci USA 2005; 102(11):4006-9.

19. Selbach M, Schwanhausser B, Thierfelder N, Fang Z, Khanin R, Rajewsky N. Widespread changes in protein synthesis induced by microRNAs. Nature 2008; 455(7209):58-63.
20. Baek D, Villen J, Shin C, Camargo F D, Gygi S P, Bartel D P. The impact of microRNAs on protein output. Nature 2008; 455(7209):64-71.
21. Lin X, Morgan-Lappe S, Huang X, et al. 'Seed' analysis of off-target siRNAs reveals an essential role of Mcl-1 in resistance to the small-molecule Bcl-2/Bcl-XL inhibitor ABT-737. Oncogene 2007; 26(27):3972-9.
22. Betel D, Wilson M, Gabow A, Marks D S, Sander C. The microRNA.org resource: targets and expression. Nucleic Acids Res 2008; 36(Database issue):D149-53.
23. John B, Enright A J, Aravin A, Tuschl T, Sander C, Marks D S. Human MicroRNA targets. PLoS Biol 2004; 2(11): e363.
24. Tse C, Shoemaker A R, Adickes J, et al. ABT-263: a potent and orally bioavailable Bcl-2 family inhibitor. Cancer Res 2008; 68(9):3421-8.
25. Xu J, Liao X, Wong C. Down-regulations of B-cell lymphoma 2 (Bcl-2) and myeloid cell leukemia sequence 1 (Mcl-1) by MicroRNA 153 induce apoptosis in a glioblastoma cell line DBTRG-05MG. Int J Cancer 2009.
26. Kertesz M, Iovino N, Unnerstall U, Gaul U, Segal E. The role of site accessibility in microRNA target recognition. Nat Genet 2007; 39(10):1278-84.
27. Kumar M S, Lu J, Mercer K L, Golub T R, Jacks T. Impaired microRNA processing enhances cellular transformation and tumorigenesis. Nat Genet 2007; 39(5):673-7.
28. Kota J, Chivukula R R, O'Donnell K A, et al. Therapeutic microRNA delivery suppresses tumorigenesis in a murine liver cancer model. Cell 2009; 137(6):1005-17.
29. Esquela-Kerscher A, Trang P, Wiggins J F, et al. The let-7 microRNA reduces tumor growth in mouse models of lung cancer. Cell Cycle 2008; 7(6):759-64.

What is claimed is:

1. A panel of primers or probes for determining an miRNA profile in a biological sample, the panel comprising:
   at least two miRNA primers or probes, each primer or probe capable of selectively binding one of at least two human miRNA selected from SEQ ID NOS: 1-19; and
   a solid support, wherein the primers or probes are probes immobilized on the solid support to form an array.

2. A panel of primers or probes according to claim 1, wherein the solid support comprises one or more components selected from the group consisting of: a membrane, a chip, a disk, a strip, a filter, a microsphere, a slide, a multiwell plate, a bead, or an optical fiber.

3. A kit useful for assaying miRNA expression levels in a biological sample of a subject, the kit comprising: a) a panel of two or more oligonucleotide primers or probes, each primer or probe capable of selectively binding a human miRNA selected from the group consisting of: SEQ ID NOS: 1-19; b) one or more reagents for amplifying the miRNA present in the biological sample using the primers or probes; and c) instructions for quantifying expression levels of the miRNA in the biological sample and evaluating the sensitivity of the subject to treatment with a Bcl-2 family protein inhibitor based on the expression levels of the miRNA.

4. The kit of claim 3, wherein the one or more miRNAs are selected from the group consisting of SEQ ID NOS: 1-12.

5. The kit of claim 3, wherein the one or more miRNAs are selected from the group consisting of SEQ ID NOS: 1-10.

6. The kit of claim 3 further comprising a solid support, wherein the probes or primers comprise probes immobilized on the solid support.

7. The kit of claim 6, wherein the solid support comprises one or more components selected from the group consisting of: a membrane, a chip, a disk, a strip, a filter, a microsphere, a slide, a multiwell plate, a bead, or an optical fiber.

8. The kit of claim 3, wherein the biological sample is selected from the group consisting of: a cell lysate, a cell culture, a cell line, a tissue, a biological fluid, a blood sample, a serum sample, a plasma sample, a urine sample, and a skin sample.

9. The kit of claim 3, wherein the one or more reagents comprise one or more miRNA hybridization or amplification reagents for any two or more of the miRNAs.

* * * * *

UNITED STATES PATENT AND TRADEMARK OFFICE
CERTIFICATE OF CORRECTION

PATENT NO.        : 8,742,083 B1                                  Page 1 of 1
APPLICATION NO.   : 12/978086
DATED             : June 3, 2014
INVENTOR(S)       : Semizarov et al.

It is certified that error appears in the above-identified patent and that said Letters Patent is hereby corrected as shown below:

In the Claims

Column 37, line 43, claim 1: "primers or probes are probes" to read as --primers or probes are--

Signed and Sealed this
Fifteenth Day of September, 2015

Michelle K. Lee
*Director of the United States Patent and Trademark Office*

```
                          SEQUENCE LISTING

<160> NUMBER OF SEQ ID NOS: 44

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugcauaguc acaaaaguga uc                                                  22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cacuggcucc uuucugggua ga                                                  22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
aacuggccua caaaguccca gu                                                  22

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uuacaguugu ucaaccaguu acu                                                 23
```

```
<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aaguucuguu auacacucag gc                                            22

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
uggugguuua caaaguaauu ca                                            22

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cgcgggugcu uacugacccu u                                             21

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
cugcaaaggg aagcccuuuc                                               20

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uacaguacug ugauaacuga a                                             21

<210> SEQ ID NO 10
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ugccuggguc ucuggccugc gcgu                                          24
```

-continued

```
<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uaaaucccau ggugccuucu ccu                                              23

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
cguuugccac uaaccucaac cu                                               22

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
augguuccgu caagcaccau gg                                               22

<210> SEQ ID NO 14
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugguugacca uagaacaugc gc                                               22

<210> SEQ ID NO 15
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ucaaaugcuc agacuccugu ggu                                              23

<210> SEQ ID NO 16
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gcugguuuca uauggugguu uaga                                             24

<210> SEQ ID NO 17
<211> LENGTH: 22
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
cugguuucac augguggcuu ag                                              22

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ugagcccugu ccucccgcag                                                 20

<210> SEQ ID NO 19
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
ccaguuaccg cuuccgcuac cgc                                             23

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cuguacaggc cacugccuug c                                               21

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uacucaggag aguggcaauc ac                                              22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uaugucugcu gaccaucacc uu                                              22

<210> SEQ ID NO 23
<211> LENGTH: 22
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 23
aaggagcuca cagucuauug ag                                                  22

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
ugugacagau ugauaacuga aa                                                  22

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uuguacaugg uaggcuuuca uu                                                  22

<210> SEQ ID NO 26
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
ggcagguucu cacccucucu agg                                                 23

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
uuuggucccc uucaaccagc ua                                                  22

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcatcgaacc attagcagat t                                                   21

<210> SEQ ID NO 29
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 29
uagcaccauu ugaaaucagu guu                                               23

<210> SEQ ID NO 30
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ucccugagac ccuuuaaccu guga                                              24

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gagaacagga aaguggccag ua                                                22

<210> SEQ ID NO 32
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
auaguugacu uuuaaccaac cacca                                             25

<210> SEQ ID NO 33
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
gacuguaagc cucaguacug ua                                                22

<210> SEQ ID NO 34
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gaacaaaucu gauaacuaug cag                                               23

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 35
agaacaggaa aguggccagu a                                              21

<210> SEQ ID NO 36
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gaaaguggcc aguagccagg caa                                            23

<210> SEQ ID NO 37
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uacccuuuug aacuuugcaa                                                20

<210> SEQ ID NO 38
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uguaaaugua uuuguaaaaa uuguau                                         26

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
acgaauugau guguaacugu au                                             22

<210> SEQ ID NO 40
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ugguucuggu uaaacagcug uac                                            23

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
```

-continued

```
tcatagaatt gattacccgc c                                              21

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
aaagttacaa gtaatagaac ta                                             22

<210> SEQ ID NO 43
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caaagttcag tttcagcaac aa                                             22

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
atggaggagg acttttagat tta                                            23
```